United States Patent [19]
Foxlin

[11] Patent Number: 5,645,077
[45] Date of Patent: Jul. 8, 1997

[54] INERTIAL ORIENTATION TRACKER APPARATUS HAVING AUTOMATIC DRIFT COMPENSATION FOR TRACKING HUMAN HEAD AND OTHER SIMILARLY SIZED BODY

[75] Inventor: Eric M. Foxlin, Cambridge, Mass.

[73] Assignee: Massachusetts Institute of Technology, Cambridge, Mass.

[21] Appl. No.: 261,364

[22] Filed: Jun. 16, 1994

[51] Int. Cl.$^6$ .................................................. A61B 5/103
[52] U.S. Cl. ........................................ 128/774; 128/782
[58] Field of Search ........................... 128/774, 782; 73/505; 364/453; 600/26; 33/333, 355 R

[56] References Cited

U.S. PATENT DOCUMENTS

| | | | |
|---|---|---|---|
| 3,786,458 | 1/1974 | Horner et al. | 128/782 X |
| 4,197,855 | 4/1980 | Lewin | 128/782 X |
| 5,181,181 | 1/1993 | Glynn | 364/566 |
| 5,203,346 | 4/1993 | Fuhr et al. | 128/782 X |
| 5,373,857 | 12/1994 | Travers et al. | 128/782 |
| 5,373,858 | 12/1994 | Rose et al. | 128/782 |
| 5,425,750 | 6/1995 | Moberg | 128/782 X |

OTHER PUBLICATIONS

D. K. Bhatnagar, "Position Trackers for Head Mounted Display Systems: A survey," Mar. 29th, 1993.

M. Koifman and S.J. Merhav, "Autonomously Aided Strapdown Attitude Reference System," Journal of Guidance and Control, vol. 14, No. 6, 1991, pp. 1164–1172.

M. Friedman, T. Starner, A. Pentland, "Synchronization in Virtual Realities," MIT Media Lab Vision and Modeling Group Technical Report No. 157, Jan. 1991.

J. Liang, C. Shaw and M. Green, "On Temporal-Spatial Realism in the Virtual Reality Environment," Proceedings of the ACM Symposium on User Interface Software and Technology, Nov. 13–11, 1991, pp. 19–25.

U.H. List, "Nonlinear Prediction of Head Movements for Helmet-Mounted Displays," Air Force Human Resources Laboratory, Technical Paper 83–45, Dec. 1983.

F. J. Ferrin, "Suvery of Helmet Tracking Technologies", SPIE vol. 1456, Large-Screen-Projection, Avionic, and Helmet-Mounted Displays, 1991, pp. 86–94.

K. Meyer, H.L. Applewhite and F.A. Biocca, "A Survey of Position Trackers," Presence, vol.1, No. 22, Spring 1992, pp. 173–200.

A. Lawrence, *Modern Inertial Technology*, Springer-Verlag, 1992, pp. 1–23.

Watson Industries, Inc., Attitude and Heading Reference System #AHRS–C300A, Owner's Manual.

Gyration, Incorporated: An Overview of the Company, Technology, and Products.

*Primary Examiner*—Sam Rimell
*Attorney, Agent, or Firm*—Steven J. Weissburg

[57] ABSTRACT

A self contained sensor apparatus generates a signal that corresponds to at least two of the three orientational aspects of yaw, pitch and roll of a human-scale body, relative to an external reference frame. A sensor generates first sensor signals that correspond to rotational accelerations or rates of the body about certain body axes. The sensor may be mounted to the body. Coupled to the sensor is a signal processor for generating orientation signals relative to the external reference frame that correspond to the angular rate or acceleration signals. The first sensor signals are impervious to interference from electromagnetic, acoustic, optical and mechanical sources. The sensors may be rate sensors. An integrator may integrate the rate signal over time. A drift compensator is coupled to the rate sensors and the integrator. The drift compensator may include a gravitational tilt sensor or a magnetic field sensor or both. A verifier periodically measures the orientation of the body by a means different from the drift sensitive rate sensors. The verifier may take into account characteristic features of human motion, such as stillness periods. The drift compensator may be, in part, a Kalman filter, which may utilize statistical data about human head motion.

44 Claims, 14 Drawing Sheets

INERTIAL ORIENTATION TRACKER APPARATUS HAVING AUTOMATIC DRIFT COMPENSATION FOR TRACKING HUMAN HEAD AND OTHER SIMILARLY SIZED BODY

GOVERNMENT RIGHTS

The U.S. Government has certain rights in this invention pursuant to Contract No. AFOSR-90-0020-B, awarded by the Air Force Office Scientific Research and Contract No. NASA NCC 2-771, awarded by the National Aeronautics and Space Administration.

BACKGROUND

In connection with many aspects of man and machine interaction, it is important to track the motions of parts of a human body. For instance, in virtual reality ("VR") applications, the problem of making a fast, accurate, and economical head-tracker that operates throughout a large workspace is crucial. It is also important for other head-mounted display ("HMD") applications. Extensive research has been devoted to the development of optical, magnetic, acoustic and mechanical tracking systems, but head-trackers are still one of the weakest links in existing virtual-environment systems. The fastest and potentially most accurate trackers are mechanical, but these are typically clumsy and range-restrictive. The largest tracking range has been achieved at the University of North Carolina by optoelectronic methods, but this type of system is extremely expensive and difficult to install, calibrate, and maintain. This type of optical tracker is sometimes referred to as an "inside-out" tracker, because a camera that is mounted on the user is aimed out toward light sources mounted on the ceiling. Ultrasonic trackers are inexpensive, but must sacrifice speed to achieve reasonable range and are sensitive to acoustical interference, reflections, and obstructions. Magnetic trackers are the most popular because of their convenience of operation (they don't even require line of sight), but the maximum range is a few feet and distortions caused by metallic objects can be problematic. For reviews of the existing four head-tracker technologies, see: Meyer, K., Applewhite, H. and Biocca, F., "A survey of position trackers," *Presence*, 1(2): 173-200, Spring 1992; Ferrin, F., "Survey of helmet tracking technologies," *SPIE*, 1456, Large-Screen-Projection, Avionic, and Helmet-Mounted Displays: 86-94, 1991; and Bhatnagar, D., *Position trackers for head mounted display systems: A survey*, technical report, University of North Carolina at Chapel Hill, March 1993, all three of which are incorporated herein by reference.

All of the known trackers (magnetic, optical, mechanical and acoustical) require interaction with another component of the apparatus that is located a distance from the body being tracked. With magnetic trackers, a magnetic field generator is provided, spaced from the tracked body. With an optical or acoustical tracker, light or sound sources are provided at known locations. Mechanical trackers are connected to a reference through an arm-like device. Thus, none provide a self-contained apparatus for mounting on the body to be tracked, which apparatus can track the orientation of the body without interaction with radiation or energy from any other apparatus. Such a self contained tracking apparatus is desirable. As used herein, a "self-contained" tracking apparatus is one that can track the orientation of a body to which it is mounted, without interaction with radiation, energy, signals, or physical connections from any other apparatus.

Another drawback with acoustic and outside-in optical trackers is that they fundamentally only measure position. Orientation is then computed from the positions of three fixed points on the head. (By "orientation" it is meant herein the rotational alignment relative to an external reference frame.) Therefore, the angular resolution is limited by the uncertainty in the position measurements as well as the distance between the three fixed points on the head. With 100 mm spacing between the fixed points, a positional jitter of $\pm 1.0$-mm causes an orientational jitter of up to $\pm 1.1°$. Additionally, since the position tracker is essentially part of the angular orientation tracker, it is not possible to meet independent specifications for the orientation tracker relative to the specifications for the position tracker.

It is also important to track other body members for other aspects of man and machine interaction. Most machines require a user instruction input device, typically actuated by the user's hand. The head, feet, torso and other body parts may also provide input instructions. Persons with special needs, such as paralysis of certain limbs, often use head and leg motions to complete tasks more typically conducted by hand motions.

Inertial navigation systems ("INS") using accelerometers and rate gyroscopes have been used for decades for ships, planes, missiles and spacecraft. Typically, such apparatus have been rather large, at least on the order of 8-10 cm in diameter and twice that in length, weighing on the order of 10 kg. An inertial navigation system is a type of self contained tracking apparatus, as that term is used herein. By "inertial apparatus", it is meant an apparatus that measures its own motion relative to an inertial reference frame through the measurement of acceleration.

A basic type of INS is called Strapdown INS, and consists of three orthogonal accelerometers and three orthogonal rate gyros fixed to the object being tracked. The orientation of the object is computed by jointly integrating the outputs of the rate gyros (or angular rate sensors), whose outputs are proportional to angular velocity about each axis. The position can then be computed by double integrating the outputs of the accelerometers using their known orientations. If the actual acceleration is $\vec{\alpha}$ and the acceleration of gravity is $\vec{g}$, then the acceleration measured by the triaxial accelerometers will be $\vec{\alpha}_{measured} = \vec{\alpha} + \vec{g}$. To obtain the position it is necessary to know the direction and magnitude of $\vec{g}$ relative to the tracked object at all times in order to double integrate $\vec{\alpha} = \vec{\alpha}_{measured} - \vec{g}$. Detailed information about inertial navigation systems is available in the literature, such as Broxmeyer, C., *Inertial Navigation Systems*, McGraw-Hill, New York, (1964); Parvin, R., *Inertial Navigation*, Van Nostrand, Princeton, N.J. (1962); and Britting, K., *Inertial Navigation Systems Analysis*, Wiley-Interscience, New York (1971), which are incorporated herein by reference.

A difficulty with using gyroscopes for head-orientation tracking is drift. Drift arises from integrating over time, a signal that is noisy, or has a bias. Drift would make the virtual world appear to gradually rotate about the user's head even when the user is not moving. By measuring the output of an angular rate sensor while it is at rest, it is possible to know its output bias and subtract the bias from all subsequent measurements. However, there is inevitably some random noise produced by the sensor in addition to its bias. In the short term, the angular drift is a random walk with RMS value growing proportional to $\sqrt{t}$. However, the small bias that remains even in a well-calibrated system leads to a drift error that grows as t, which will eventually exceed the Brownian Motion error that grows as $\sqrt{t}$.

U.S. Pat. No. 5,181,181, issued on Jan. 19, 1993, to Glynn, for "Computer Apparatus Input Device for Three-Dimensional Information," discloses a computer input mouse, which senses six degrees of motion using three accelerometers for sensing linear translation and three angular rate sensors for sensing angular rotation about three axes. The disclosure does not acknowledge or address the problem of drift.

Complete virtual environment systems also suffer from a problem that is not directly related to the problem of tracking body member motions and orientations. A great deal of graphical rendering is required to present to the user a visual image of the environment being simulated. The view to be presented depends on the user's orientation and position. The rendering requires significant computation, which is time consuming. Typically, the computation can not begin until the orientation is known. Thus, the speed of information acquisition is extremely important. It would also shorten the overall system latency if a reliable method of predicting the user's orientation in advance existed.

OBJECTS

Thus the several objects of the invention include to track the angular orientation of the head (or other body member) with undiminished performance over an unlimited range or working volume. Another object is to track body member orientation with low latency, thus preserving the illusion of presence and avoiding simulator sickness. Another object is to track body member orientation with low output signal noise, so that it won't be necessary to reduce jitter through use of delay-ridden filters. Another object is to track body orientation without interference problems. Interference sources to be avoided include acoustical, optical, mechanical and electromagnetic. Another object of the invention is to predict what the orientation of the body member will be a short time in the future, to reduce system delays when the orientation tracker is used with other delay-inducing apparatus, such as a graphics rendering engine in a virtual environment simulator. An additional object is to resolve body member orientation without limitation due to the quality or absence of a position sensing device. Yet another object is to facilitate a modular head tracking apparatus, using independent orientation and position tracking modules, thus permitting tailoring each to independent specifications. Another object of the invention is to track the orientation of a body using a self-contained sensing apparatus, so that an unlimited number of trackers may be used in the same area simultaneously without performance degradation.

SUMMARY

In a preferred embodiment, the invention is a self contained sensor apparatus for generating a signal that corresponds to at least two of the three orientational aspects of yaw, pitch and roll of a human-scale body, relative to an external reference frame. The apparatus comprises: a self contained sensor for generating first sensor signals that correspond to rotational accelerations or rates of the body about certain axes relative to said body; a mechanism for mounting the sensor to the body and, coupled to the sensor, a signal processor for generating orientation signals relative to the external reference frame that correspond to the angular rate or acceleration signals, wherein the first sensor signals are impervious to interference from electromagnetic, acoustic, optical and mechanical sources.

In a preferred embodiment that uses rate sensors, the signal processor also includes an integrator to integrate the rate signal over time. The rate sensors may be vibrating piezoelectric devices, silicon micro-machined devices, magneto-hydrodynamic devices or optical devices, to name several.

Another preferred embodiment of the invention further includes a drift compensator, coupled to the angular rate sensor and the integrator, for compensating for any drift with respect to time in the rotational orientation signal.

According to one preferred embodiment, the drift compensator may include a gravitational tilt sensor, or a magnetic field sensor, or both.

The drift compensator, according to another preferred embodiment, includes a verifier that periodically measures the orientation of the body by a means different from using the rotational rate signal and generates an orientation drift compensation signal based on the verification measurement to reduce the effect of drift.

The verifier may take into account characteristic features of human motion, such as the existence of stillness periods. The drift compensator may be implemented using, in part, a Kalman filter, which may utilize statistical data about human head motion.

The apparatus of the invention may also include an orientation predictor, that predicts the orientation in which the body will be a short time in the future.

According to yet another preferred embodiment, the invention is an apparatus for generating a signal that corresponds to the orientation of a human-scale body, relative to a reference frame. The apparatus comprises a self contained first sensor for generating a drift sensitive orientation signal that corresponds to the rotational orientation with respect to at least two degrees of freedom of the body and is impervious to interference from electromagnetic, acoustic, optical and mechanical sources and is subject to drift over time. The apparatus also includes a self contained second sensor for generating a drift compensating orientation signal that corresponds to the rotational orientation with respect to the at least two degrees of freedom of the body and is impervious to interference from electromagnetic, acoustic, optical and mechanical sources and which is relatively impervious to drift over time, and a mounting mechanism for mounting the first sensor and the second sensor to the body. Coupled to said first sensor and said second sensor, a signal corrector means for generating a corrected rotational orientation signal based on said drift sensitive and drift compensating orientation signals.

Another preferred aspect of the invention is a method for generating a signal that corresponds to the orientation of a human-scale body, relative to a reference frame. The method comprises the step of using a first self contained sensor physically coupled to the body, generating a drift sensitive orientation signal that corresponds to the rotational orientation with respect to at least two degrees of freedom of the body and that is impervious to interference from electromagnetic, acoustic, optical and mechanical sources and is subject to drift over time. The method also includes the steps of: using a second self contained sensor physically coupled to the body, generating a drift compensating orientation signal that corresponds to the rotational orientation with respect to said at least two degrees of freedom of the body and that is impervious to interference from electromagnetic, acoustic, optical and mechanical sources and which is relatively impervious to drift over time; and generating a corrected rotational orientation signal based on the drift sensitive and drift compensating orientation signals.

According to another preferred embodiment, the method also includes, when generating the corrected rotational orientation signal, the step of taking into account characteristic aspects of human motion, such as the occurrence of periods of stillness, or statistics about head motions in particular applications.

Still another preferred embodiment of the invention is an apparatus for simulating a virtual environment that is displayed to a user. The apparatus comprises a self contained orientation sensor for generating an orientation signal, such as described above, and is impervious to interference from electromagnetic, acoustic, optical and mechanical sources, a position sensor, a mechanism for mounting the position and orientation sensors to the body member, a virtual environment generating means a means for displaying virtual environment signals to the user and means for coupling the position sensor and the orientation sensor to the virtual environment means.

BRIEF DESCRIPTION OF THE DRAWINGS

These and other features, aspects, and advantages of the present invention will become better understood with regard to the following description, appended claims and accompanying drawings, where:

DETAILED DESCRIPTION OF PREFERRED EMBODIMENTS OF THE INVENTION

In its most basic form, a preferred embodiment of the invention is an inertial angular orientation tracking apparatus. (The invention does not produce position information, only angular orientation information.) Drift sensitive sensors, such as angular rate sensors, produce a signal that is integrated to give a signal that represents angular position. The angular position signal may drift, due to integration of a bias or noise in the output of the rate sensors. To correct this drift, compensating sensors, such as gravimetric tilt sensors and sometimes also geomagnetic heading sensor(s) periodically measure the angular position, and this directly measured position signal is used to correct the drift of the integrated position signal. The direct angular position sensors cannot be used alone for dynamic applications because the gravitational sensors are also affected by non-gravitational accelerations, and therefore only accurately reflect angular position when under the influence of no non-gravitational accelerations. Some suitable compensating sensors, such as pendulous inclinometers, also take longer to settle than would be desirable for a stand alone sensor to deliver continuous orientation signals.

Typically, the drift sensitive sensors are angular rate sensors, (these include: rate gyroscopes and vibrating piezoelectric, magneto-hydrodynamic, optical and micro-machined silicon devices) the output from which are integrated once. However, other suitable drift sensitive sensors include linear accelerometers used to sense angular rate, gyroscopic angular position sensors (with no need to integrate) and angular accelerometers (integrated twice).

Similarly, typically the compensating sensors are inclinometers and compasses. However, other suitable compensating sensors include accelerometers. For purposes of simplifying the following discussion, the embodiment discussed uses angular rate sensors as the drift sensitive sensors and a z-axis inclinometer and a compass as the compensating sensors. However, the other types of sensors mentioned are also intended to be included as alternate embodiments of the invention.

The present invention may be applied toward tracking the head and other body parts with appropriate modifications. However, for simplicity, this discussion focuses on tracking the head and suitable apparatus therefore.

Figure 1:
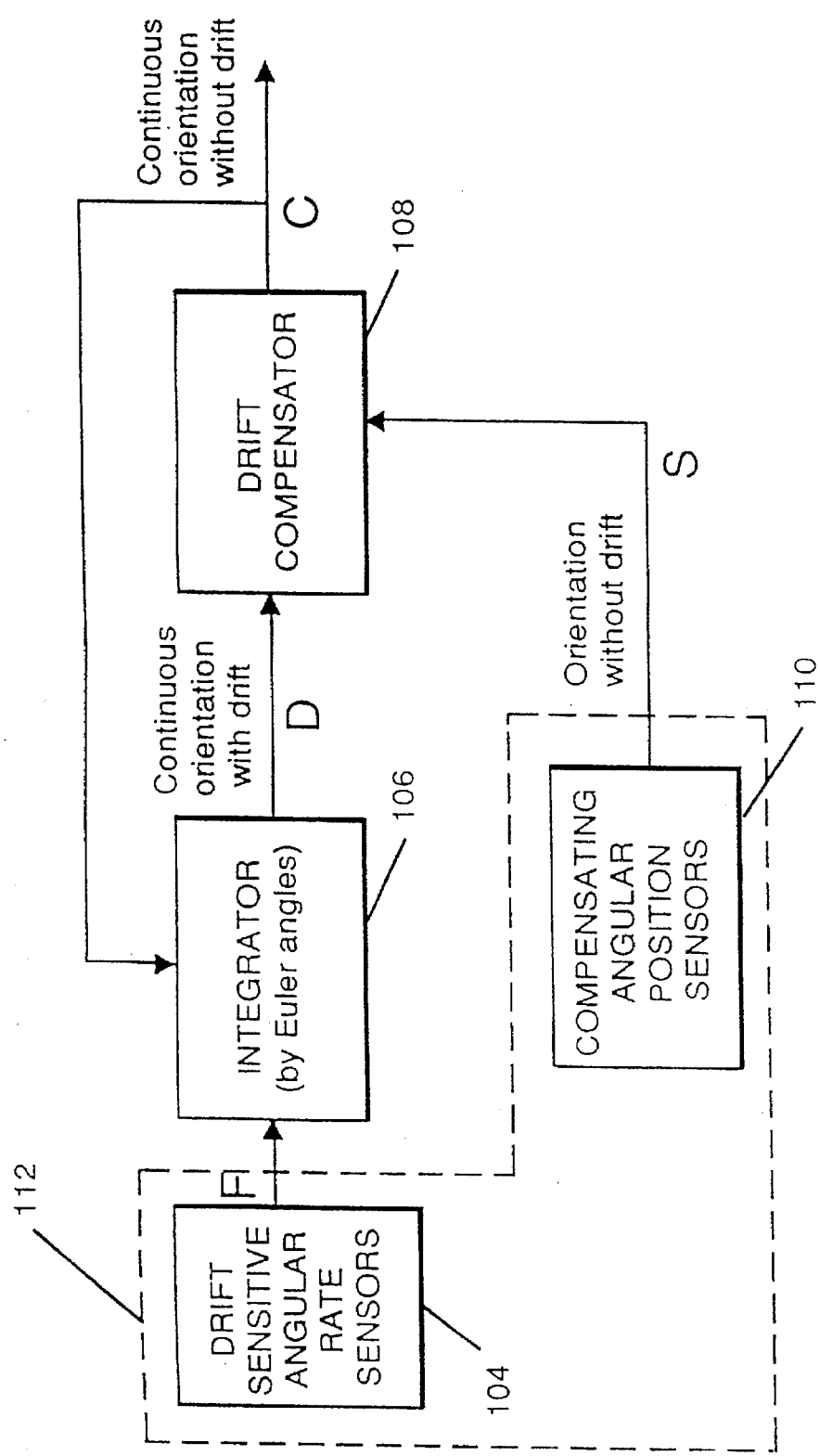
FIG. 1 is a schematic block diagram overview of a preferred embodiment of the apparatus of the invention.

A schematic configuration for a generic embodiment of the invention is shown in FIG. 1. A set of drift sensitive angular rate sensors 104 continuously generate signals F that correspond to the rate of change of the angular orientation of the individual sensors. (The sensors themselves are discussed in more detail below.) The rate sensors 104 are connected to an integrator module 106, which jointly integrates the signal F that represents the set of angular rates using a suitable method, such as the Euler method or a quaternion method or using Direction Cosine Matrices. The output of the integration module is a signal D, which represents a set of orientation angles, which correspond roughly to the orientation of the body to which the rate sensors are attached, as explained below. This orientation signal is passed to a drift compensation module 108.

A set of drift compensating angular position sensors 110 is also provided. This set of position sensors generates a signal S that is related to the angular orientation of the body to which the rate sensors are attached, as explained below. This signal S is also provided to the drift compensation module 108. The drift compensation module uses the angular position signal S to generate a signal C that represents the angular orientation corrected for errors in the angular orientation signal D output from the integrator 106, which errors may have arisen due to drift or other causes. The corrected angular orientation signal C is fed back to the integration module 106 for transforming the coordinates of the angular velocities. The corrected angular orientation signal C is also provided as an output to whatever equipment is connected to the angular orientation apparatus, requiring this information. Such equipment can comprise a virtual reality system, a computer, a teleoperator, etc.

A schematic representation of how the apparatus shown in FIG. 1 would be mounted upon a human body member, such as a head, is shown in FIG. 2. A head band 202 is worn around the user's head 210. The head band 202 supports a sensor array bracket 206 through a rigid connector 208. The sensor array bracket 206 supports three drift sensitive angular rate sensors 204r, 204p and 204y, which, together constitute the set of angular rate sensors 104, shown in FIG. 1. A two axis inclinometer 210i constitutes one of the set of compensating angular position sensors 110, shown in FIG. 1, the other being a magnetic compass 210m.

Figure 2A:
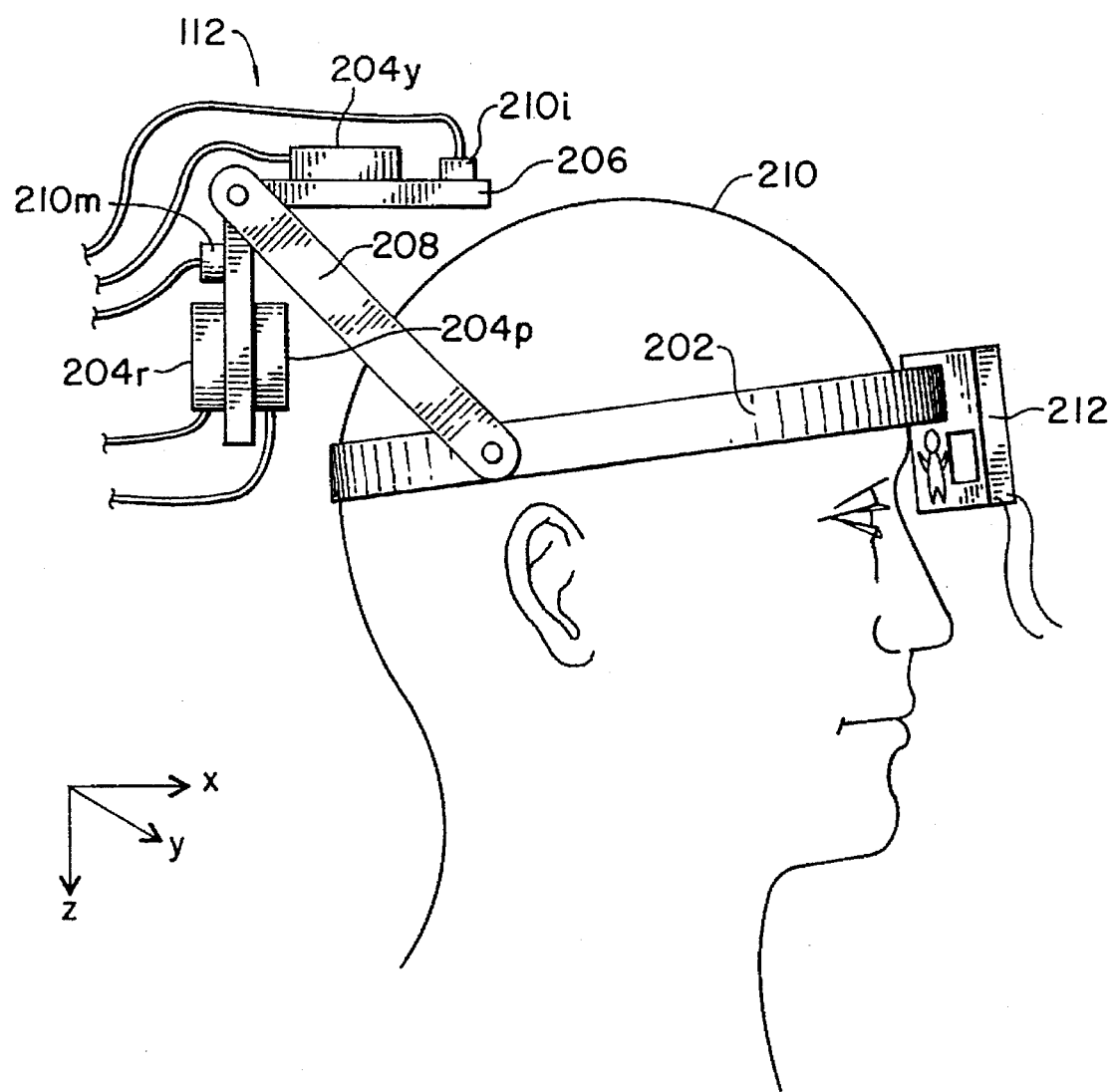
FIG. 2A is a schematic illustration of an embodiment of the apparatus of the invention mounted upon a user's head, along with a head mounted display.
Figure 2B:
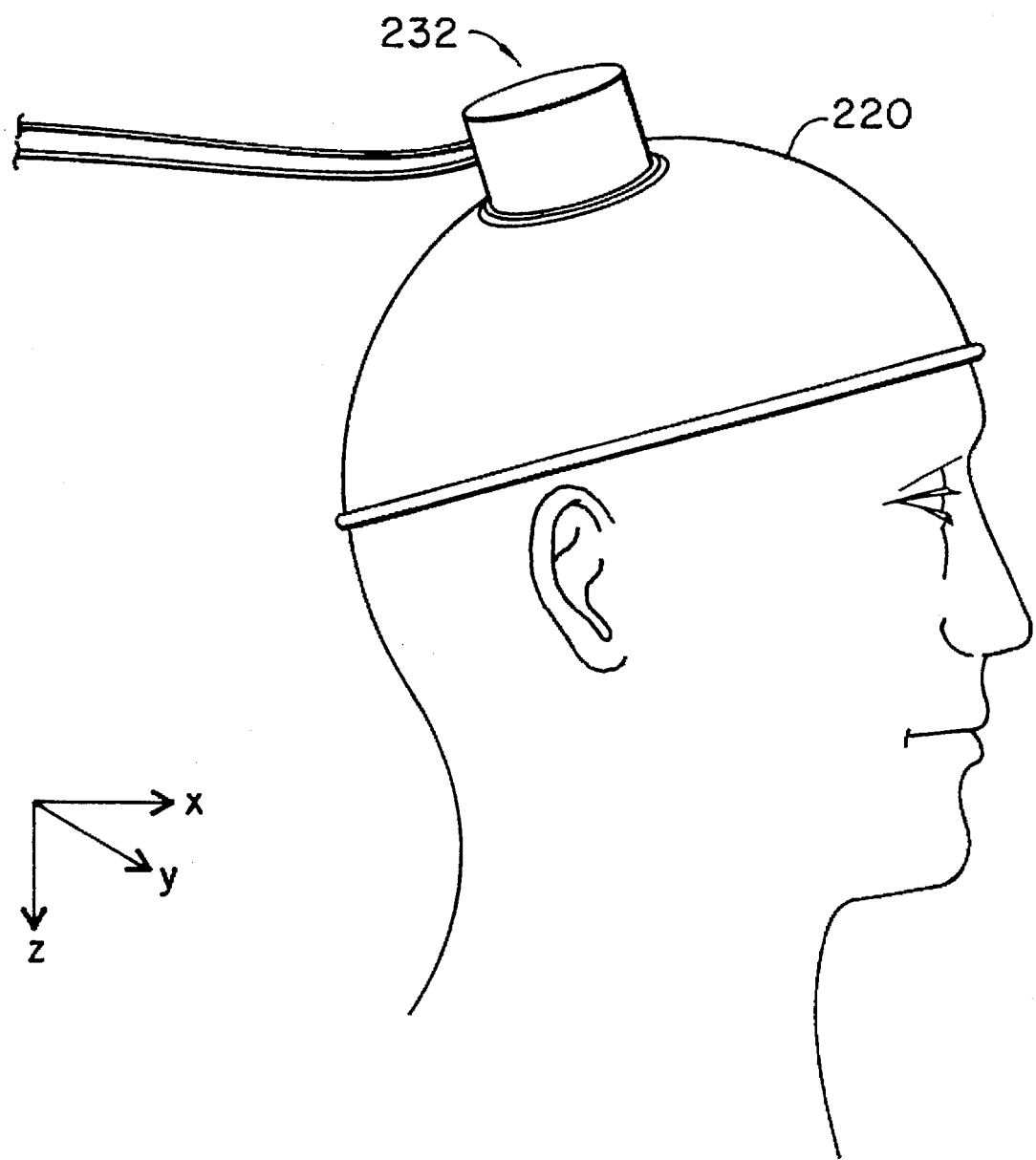
FIG. 2B is a schematic illustration of another, more compact embodiment of the apparatus of the invention, mounted on a user's head.

The support is shown schematically as an arm 208 for simplicity of discussion in FIG. 2A. However, a more practical arrangement supports all of the hardware encased in a small container 232 closer to the head, on a support surface approximately a skull cap 220 as shown in FIG. 2B. In the embodiment shown in FIG. 2B, all of the sensors are arranged in the container 232 in an orientation that is suitable for measuring the desired orientation and rates. The arrangement of the components as shown in FIG. 2A is convenient for discussion and is referred to below.

For some applications of the apparatus of the invention, a display unit 212 may be provided, which is controlled by a display controller, not shown, which uses the angular orientation information generated by the apparatus of the invention to generate images, such as a representation of a room with a representation of the user passing therethrough. Such a head mounted display ("HMD") is not necessary, for instance, in non-virtual reality applications where the head is simply used for giving input instructions to a machine or computer. Such uses include input devices for individuals who have lost use of their hands or feet.

In one preferred embodiment, the drift sensitive angular rate sensors 104 are three orthogonally-mounted integrated circuit rate gyros, sold by Systron-Donner Inertial Division of Concord Calif., under the tradename "GyroChips." Each rate gyro produces a DC voltage output linearly proportional to angular velocity in the range ±1000°/s. The drift compensating angular position sensors 110 comprise a two-axis electrolytic fluid inclinometer 210i, sold by The Fredericks Co. of Huntington Valley, Pa., under the trade designation 0717, and a fluxgate compass 210m, sold by Etak of Menlo Park, Calif., under the trade designation 02-0022. The inclinometer 210i is a gas bubble in a liquid, ¼" in diameter, with five electrodes to sense resistance changes when the bubble is tilted in either the front-back or right-left direction. A small electronic circuit converts the resistance changes to voltage signals that correspond to the angular orientation in both the front-back direction and the right-left direction.

The fluxgate compass 210m measures magnetic field strength in two orthogonal horizontal directions. Theoretically, one magnetic field component, combined with the known tilt, provides enough information to compute heading direction (yaw). However, one or two additional axes may be provided to enhance the robustness of the measurement and/or the simplicity of computation. The fluxgate compass generates an electrical signal that corresponds to the angular yaw orientation, i.e., about the yaw axis, that is vertical, relative to the room, as shown.

The integrator performs an integration, such as by Euler angles or quaternions, upon the drift sensitive angular rate signals F, to generate a signal that corresponds to the angular orientation, attributable to the continuous angular rate measurements. In the Euler angle method, the body-referenced angular rates are first converted to Euler angle derivatives, using the following well known equations:

$$\dot{\psi} = P + Q\sin\psi\tan\theta + R\cos\psi\tan\theta \quad (1)$$

$$\dot{\theta} = Q\cos\psi - R\sin\psi \quad (2)$$

$$\dot{\phi} = Q\sin\psi\sec\theta + R\cos\psi\sec\theta \quad (3)$$

Where P, Q and R represent the angular velocities of an object around the x, y and z axes fixed to the object, respectively. According to the coordinate convention used in aeronautics, the x-axis points forward, y points right, and z points down. P, Q, and R can be thought of as the outputs of three orthogonal angular rate sensors mounted on the object. The Euler angles $\phi, \theta$ and $\psi$, respectively, represent yaw, pitch, and roll angles, which are defined as the amount of counterclockwise rotation applied about the z, y, and x body-axes in that sequence (starting from a known initial orientation) to get to the body's current orientation. The sequence of applying the rotations matters. In other words, the operation of rotation in 3 dimensions is not commutative.

Equations 1–3 provide the rates of change of the Euler angles, which can then be integrated by the integrator 106 to obtain the updated Euler angles.

A simple, and typical procedure for integration in a computer is, after each time step $\Delta t$, to set the following:

$$\psi(t+\Delta t) = \psi(t) + \dot{\psi}(t)\Delta t \quad (4)$$

$$\theta(t+\Delta t) = \theta(t) + \dot{\theta}(t)\Delta t \quad (5)$$

$$\phi(t+\Delta t) = \phi(t) + \dot{\phi}(t)\Delta t \quad (6)$$

Alternatively, a higher order Runga-Kutta integration method may be used if needed. The increments applied at time t depend (through Equations 1–3) on the values of the Euler angles $\phi, \theta$ and $\psi$ at time t. If those values were taken simply as the values computed as the result of the previous integration step, then the accumulation of a little bit of error each cycle would cause the next increment used to be wrong, and the error drift rate would accelerate exponentially. To prevent this undesirable result, the Euler angles used in Equations 1–3 are taken from the signals output from the drift compensator 108.

According to a preferred embodiment of the invention, the compensating angular position sensors and compass are used periodically, at times when the user's head is not moving. (As mentioned, they cannot alone be used all of the time, because they provide inaccurate position signals when they are accelerating.) Head pauses normally happen at least once every ten seconds. The fluid-filled inclinometer settles to a fixed location that indicates pitch and roll orientation within about ¼ second after motion has ceased. At that moment, the absolute head orientation (with respect to the two inclinometer measured axes) is known with high accuracy. The fluxgate compass also provides a measurement of the orientation of the head with respect to the two axes that it measures, within the same ¼ second. This compass information and inclinometer information is used to reset the signals that are output from the drift compensator 108, which signals represent the angular orientation of the head. Thus all of the drift that has accumulated since the beginning, or last reset, is removed. To prevent sudden orientation shifts from jarring the user, the drift is removed from the output gradually, rather then all at once. Thus, the drift compensator 108 generates a set of signals over time that gradually approach the correct signal.

Figure 3:
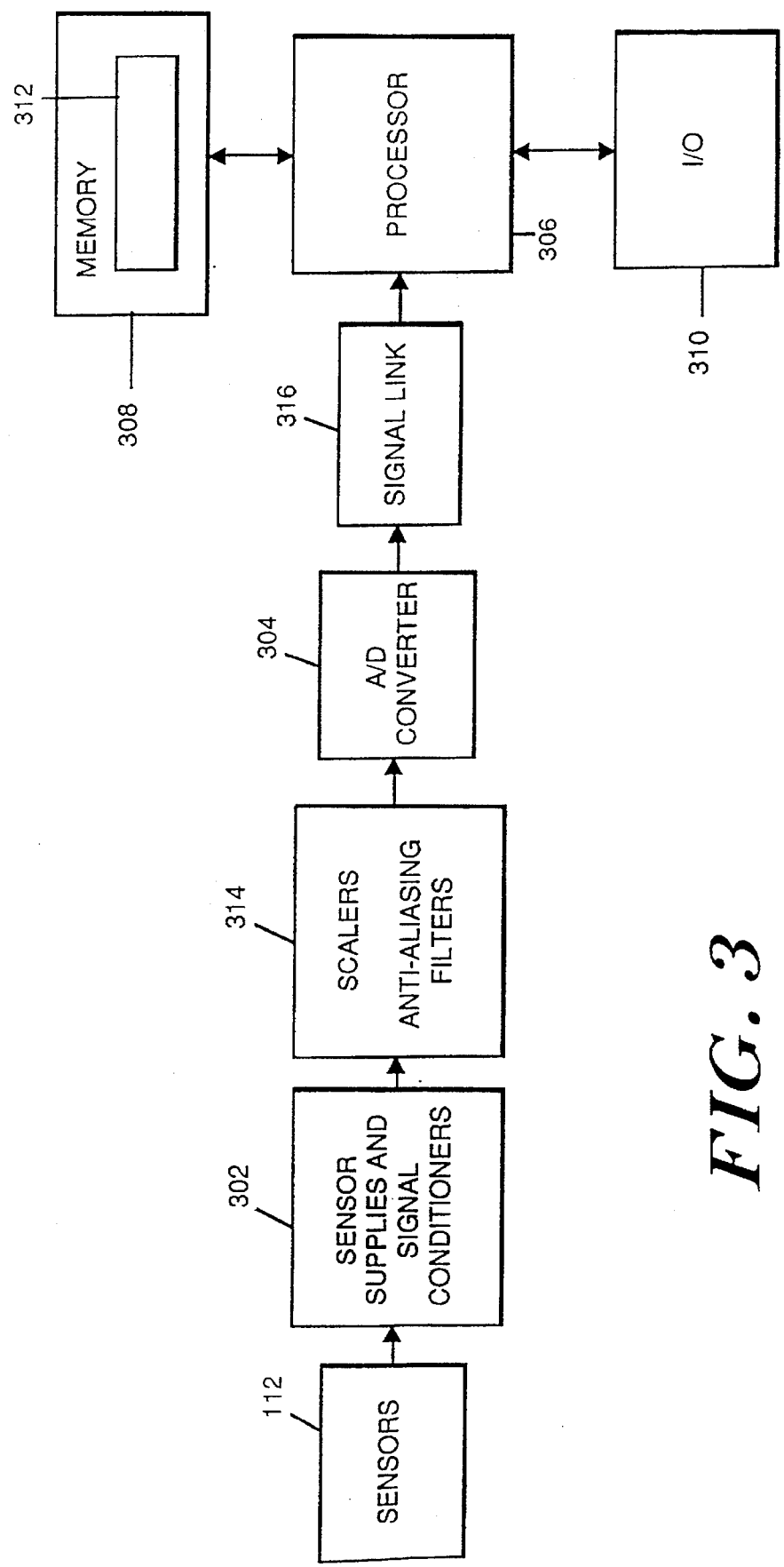
FIG. 3 is a schematic block diagram illustration of a preferred embodiment of the apparatus of the invention partially embodied by a computer with a memory and an input output device.

The sensor assembly shown in FIGS. 1, 2A and 2B is connected to analysis apparatus, as shown schematically in FIG. 3. The sensor assembly 112 consists of all the sensors shown in FIGS. 1 and 2A, firmly fixed to a bracket, with care taken to ensure the orthogonality of the three GyroChips. A prototype assembly measures 2"×2¼"×3¼" (5.1 cm×5.7 cm×8.25 cm) and weighs about 1 pound (0.4 kg). (This assembly may be too large for many applications. A second prototype has been made, which measures 2"×2"×1" (5.1 cm×5.1 cm×2.5 cm) and which weighs only 4 oz. (100 g) and may be mounted in a small container as shown in FIG. 2B. The second prototype uses angular rate sensors from JR Inc., Japan, sold under trade designation NEJ-1000. Each is ¾"×1" (1.9 cm dia.×2.54 cm) long. The NEJ-1000 uses a vibrating equilateral triangular prism with a piezoelectric ceramic vibrator on one face and piezoelectric sensors on the other two faces.

The sensors are coupled, for instance through a cable, to an electronics board 302, which provides appropriate power supplies for all the sensors, and converts all their outputs into buffered DC voltages. These signals are provided to another electronic module 314, which scales the analog signals and provides anti-aliasing filtering. A data acquisition board 304, such as is sold by Data Translation, Marlboro, Mass., under trade designation DT2814, converts the analog signals to digital signals. The data acquisition board may be installed in an Intel 80386 microprocessor based personal computer 306, with appropriate memory 308, and input/output devices 310 for user instructions. The connection 316 between the A/D converter 304 and the processor 306 may be a physical bus, or it may include a telemetry transmitter and receiver pair.

The computer is typically configured, using software, as an integrator coupled with a drift compensator, shown in FIG. 1. Suitable software that accomplishes this configuration is shown schematically by flow charts in FIGS. 4A, 4B and 4C.

Figure 4A:
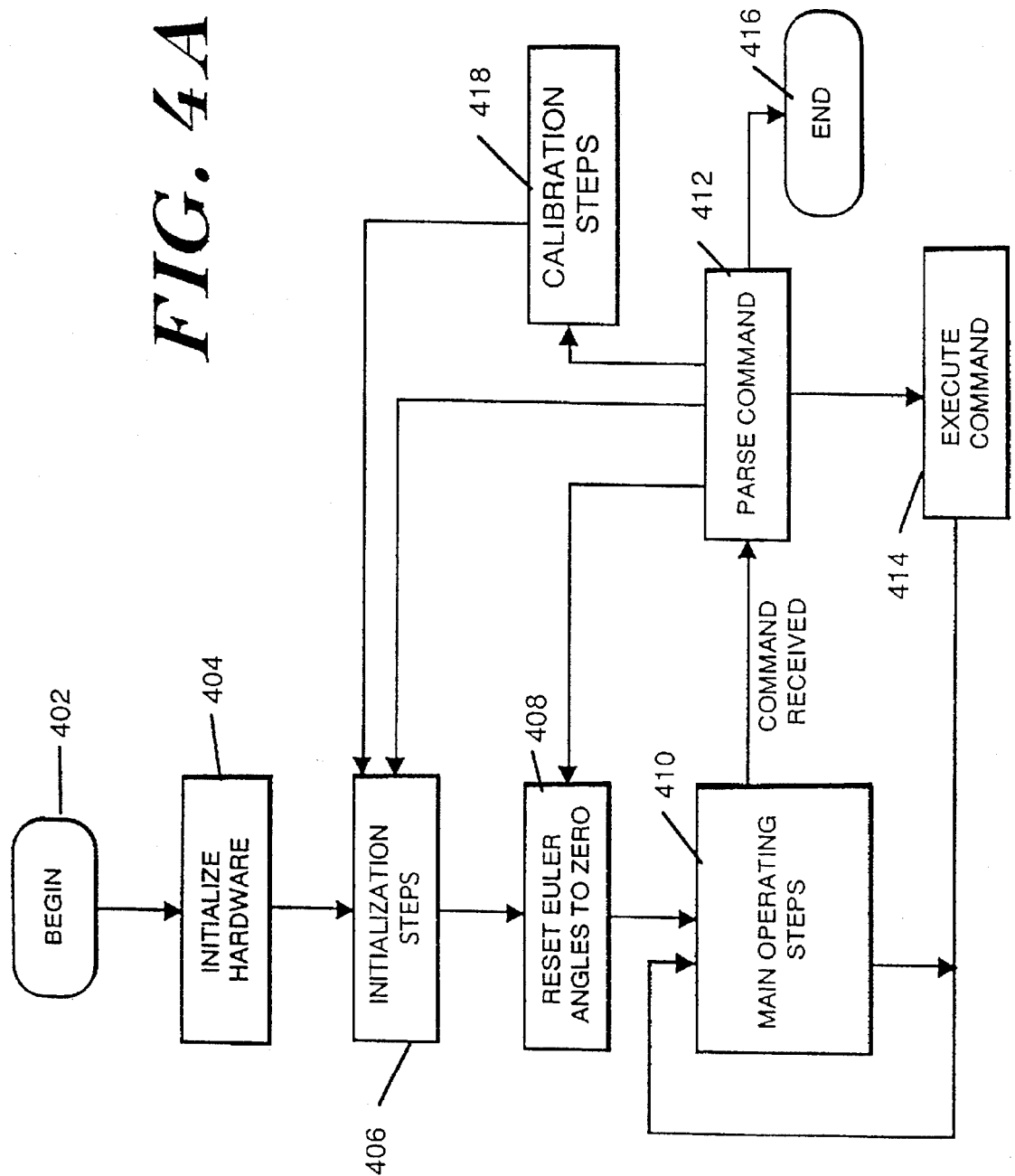
FIG. 4A is a schematic flow chart illustration of an overview of the steps of a computer program for controlling a computer, that may constitute a portion of a preferred embodiment of the apparatus of the invention.

An overall view of the operating steps of the invention is shown by the flow chart of FIG. 4A. The process begins 402 and initializes 404 the hardware. Hardware initialization includes steps such as choosing a clock speed, activating peripheral devices and setting up interrupts. Next, initialization steps 406 are conducted, shown in more detail in FIG. 4B. These steps, discussed in more detail below, establish the rest position, from which orientation is measured and measure biases for the rate sensors. After the initialization steps, the Euler angles are reset 408 to zero (as they may be non-zero after the initialization steps are performed). Next, the main operating steps 410 are performed. The operating steps are shown in more detail with reference to FIG. 4C.

The main operating steps generate a set of signals that correspond to the output orientation angles. Typically, the operating steps are repeated again and again through a loop, until a command has been received. During the execution of the operating steps, the user may generate commands, or a command may be generated by the host computer to which the orientation tracker is connected. If a command is received, as shown in the overall operation flow chart (FIG. 4A), the command is parsed 412.

Typical commands include: to change operation between metric and English units; resetting the origin; reinitializing the operation; quitting; calibration; switching between continuous reporting and demand-made reporting; etc. After parsing, the command is executed 414. Execution of some of the commands are indicated in the flow chart as separate steps, such as: to end 416; and to perform calibration steps 418. Others are indicated by routings to stages in the overall operation already identified, such as: to reinitialize 406; reset Euler angles 408; and returning to the operating steps 410.

Figure 4B:
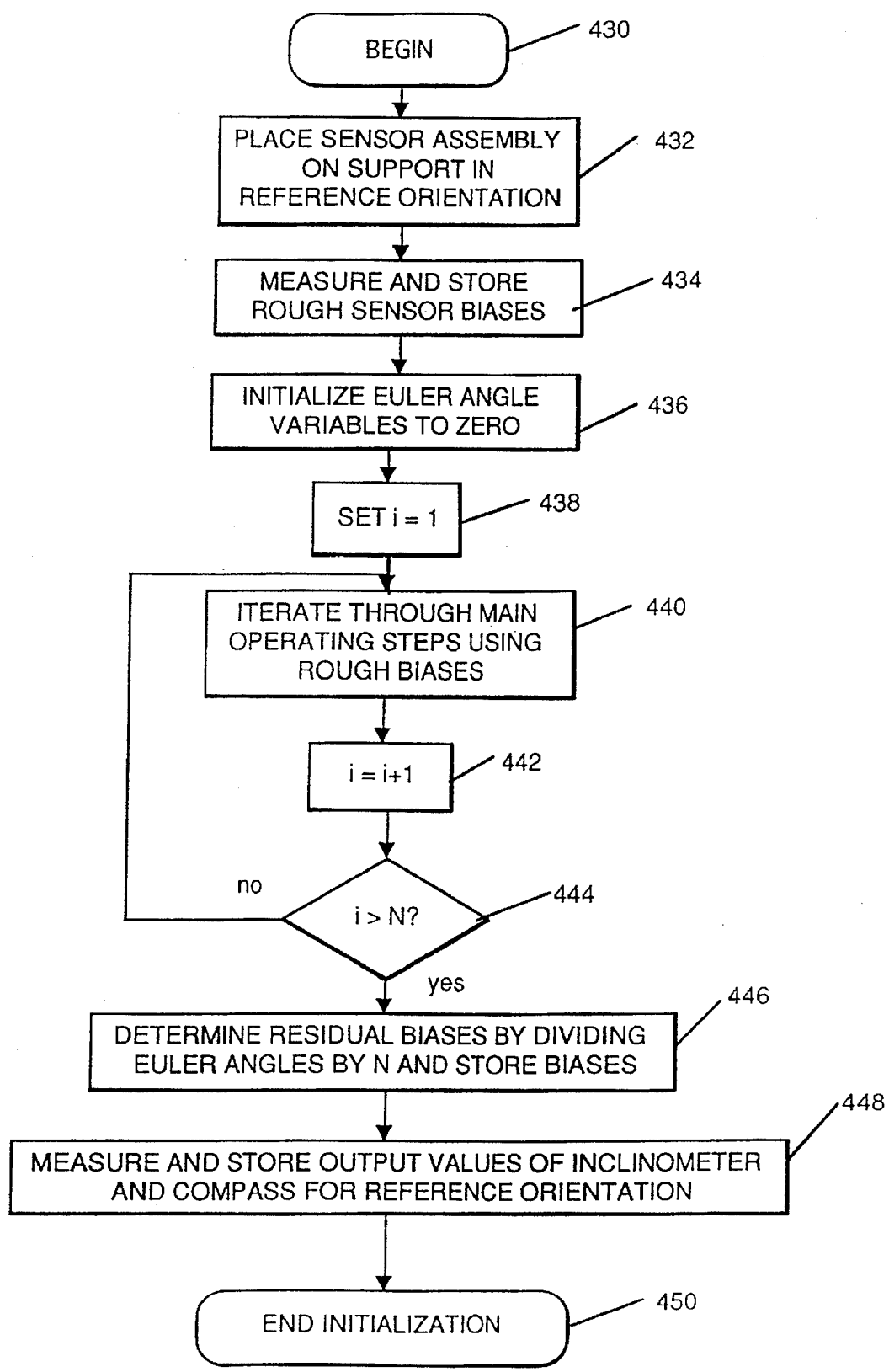
FIG. 4B is a flow chart representation of the steps of a computer program for controlling a computer to perform initialization steps.

Turning now to the initialization steps, these are shown in more detail in FIG. 4B, and begin at 430. Initialization must be conducted with the sensor assembly held stationary in a known reference orientation. In a preferred embodiment, the user is instructed 432 to place the sensor assembly in such a position by a message delivered to the apparatus input/output devices or implicitly by the fact of starting the tracker. Next, the sensor biases are measured using a rough measure and stored 434. The rough bias is typically maintained in computer memory and operations as an integer. It is measured by A/D converting the sensor signals several times in rapid succession, averaging, and storing the results. The Euler angle variables are then initialized 436 to zero. An iteration is then conducted for a set number N of cycles (or for a certain time). The iteration runs 440 through the main operating steps, shown in detail in FIG. 4C and discussed below, a number of times, using the rough bias. After the prescribed number or time has been reached 444, residual biases are determined 446, by dividing the final values for the Euler angles output from the apparatus by the number of cycles N and storing these residual biases. The residual biases are a fine adjustment which must be added to the rough biases each time they are used to insure minimum drift rate. (The rough bias measurements are not sufficiently accurate, due to limited conversion resolution and also because they do not reflect the accumulated numerical errors in the integration steps.) Finally, running averages of the signals output by the inclinometer 210i and the compass 210m, that have been maintained throughout the initialization stage, are stored. The initialization steps then end 450.

Figure 4C:
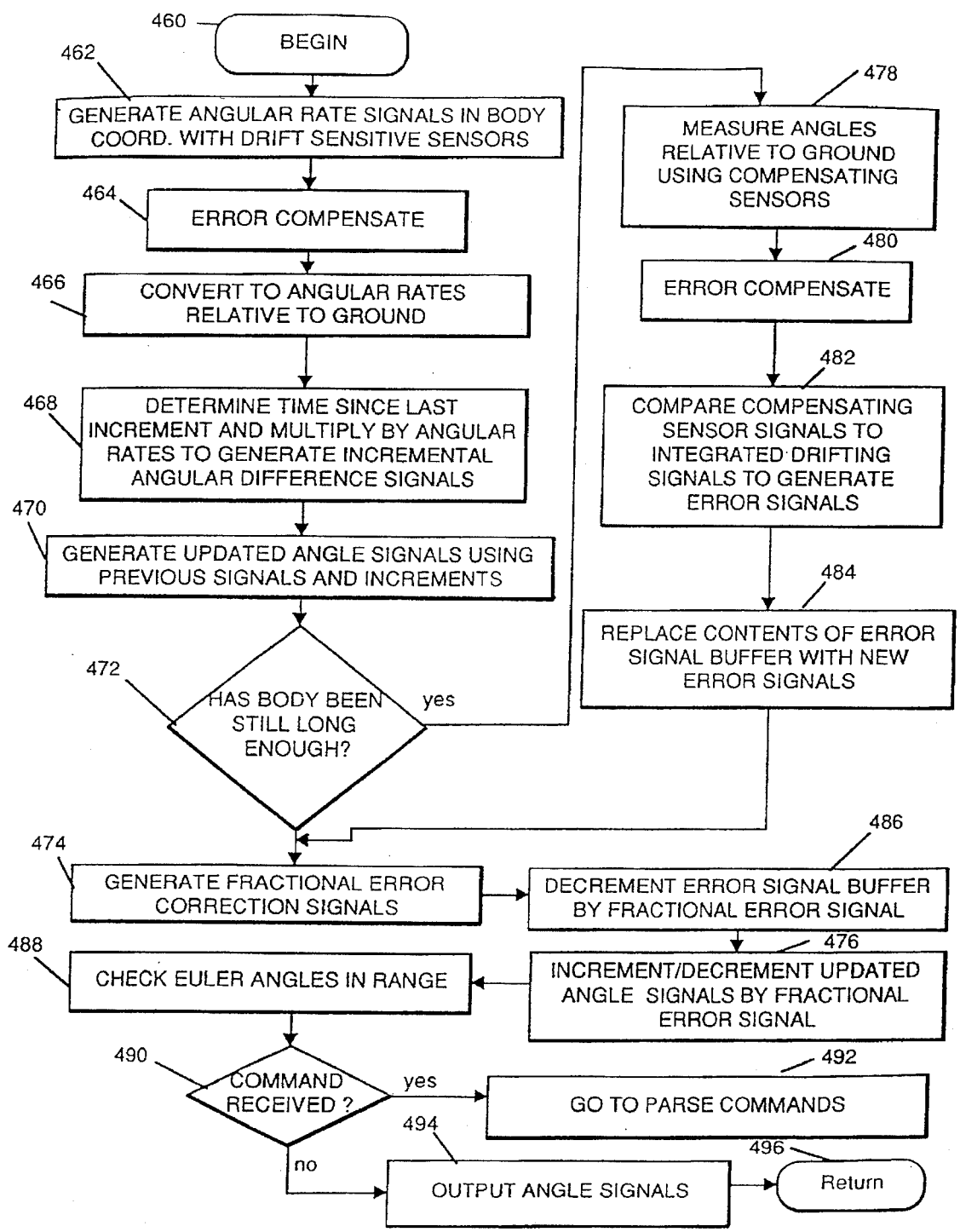
FIG. 4C is a flowchart representation of the steps of a computer program for controlling a computer to perform the main operating steps of measuring Euler angles and compensating for drift.

The main operating mode steps 410 are shown in more detail in FIG. 4C, which begin at 460. Signals that represent the angular rate of motion of the body in coordinates referenced to the body are generated 462 with the angular rate sensors 204. In a preferred embodiment, this step is implemented by the processor 306 sending a command to the A/D convertor 304 to trigger conversion, waiting for the end of the conversion by the A/D convertor, reading a signal in from a buffer and converting the digital signal into an appropriate numerical representation of angular velocities.

Compensation is made 464 for certain types of "errors" typical of angular rate sensors. These types of errors include temperature sensitivity, acceleration sensitivity, bias, scale factor, misalignment, cross-axis sensitivity, nonlinearity, hysteresis, etc. Compensation is made using parameters measured during the calibration 418 and initialization 406 steps. Then, the angular rates are converted 466 to angular rates relative to a ground based reference system (Euler angle rates), using the relations set forth in Eq. 1–3. From the Euler angle derivative signals generated by the conversion step 466, an incremental angular difference signal is generated 468. This signal corresponds to the angular rate of change, times a time interval, such as $\dot{\theta}(t) \times \Delta t$. (The time interval must first have been determined by comparing the present time to the time at the last rate measurement.)

The incremental angular difference is used to generate 470 a signal that corresponds to the angular orientation, using the relations shown in equations 4–6. This angular orientation signal will be subject to drift, due to the fact that a previously generated signal $\theta(t)$ is used to generate a subsequent signal $\theta(t+\Delta t)$. If there is an error in the signal, it will be perpetuated.

Next, the method entails the step of determining 472 when the output signals of the compensating angular position sensors 110, such as the tilt bubble sensor, are reliable, and using these signals to update compensating signals that are used in the following, update Euler angles, step 476 to compensate for drift. The signals from the compensating position sensors are taken as reliable when they have been nearly constant for a set period of time, for instance, for the bubble sensor, ¼ second, and when all three angular rate sensors 104 have been sufficiently close to zero for that same period of time. This is determined at the decision step 472.

If, at the decision step 472 the criteria for stillness have been met, the apparatus branches to the compensating position measurement steps 478 and following. If the stillness criteria have not been met, the apparatus branches to the step 474 for generating a different sort of error signal.

Turning first to the case where the sensors have remained still for a suitable time, the signals generated by the inclinometer and the compass are taken and the angular orientation is generated 478 from those signals, based on the particularities of the type of compensating sensors used. Waiting ¼ second after the outputs stop changing not only assures that the readings used are very stable, but also allows averaging of many readings to obtain much better precision than a single reading with 12-bit conversion would accomplish. If on a particular iteration the still time reaches ¼ second, the averages accumulated over the past ¼ second are converted into actual pitch and roll angles using look-up tables 312 stored in the memory 308 to compensate for any sensor nonlinearities.

Next, compensation is taken 480 for errors inherent to the compensating angular position sensors 110 of the same character as the errors inherent to the drifting angular rate sensors 104. This compensation is taken in the same manner.

Once compensation has been made to the raw signal, the angles so indicated are compared 482 to the angular orientation signals that the apparatus has obtained at 470 from the drift sensitive angular rate sensors 104 and an error signal is generated. This error signal is placed 484 in an error signal buffer memory (typically configured as a region of the general memory 308).

Turning now to the steps that the apparatus follows to actually correct for the drift, the steps join the main stream of steps following the stillness determination 472, to generate 474 a fractional error correction signal. This fractional error signal is less than the entire error signal, as explained below. The fractional error signals are added 476 to the updated Euler angle signals generated at step 470. The algebraic sign of the error signal is chosen so that when added to the Euler angle, the sum is closer to the actual angular position than was the previous Euler angle. A fractional error correction signal is used, rather than the entire error correction signal, to prevent a "jump" or "lurch" apparent to the user when the error correction is made. The fractional error signal is also used to reduce 486 the error signal maintained in the error signal buffer, so that the error signal is continually reduced in the error signal buffer until nothing remains to be added to the updated Euler angle signals.

A preferred method to generate the fractional error signal is to set an increment $\delta$ (in degrees). If the actual error is greater than the increment $\delta$, then the fractional error used is $\delta$. Otherwise, the fractional error used is the actual fractional error. This provides a slow linear correction at a rate of $n\delta$ °/sec until the error is gone, where n is the number of operating mode cycles per second.

After the fractional error correction signal has been combined with the updated Euler angle signal to produce a corrected updated Euler angle signal, a check must be made 488 that the Euler angles are within range. If not, Euler angles that are within range are assigned. For a typical embodiment, the ranges are as follows: yaw ±180°; pitch ±90°; and roll ±180°.

Following the updating and the correction of the Euler angles, the main operating steps check 490 to determine whether any commands have been received from the host computer or processor. If yes, the apparatus branches 492 to the parse command step 412 of the overall operating steps shown in FIG. 4A. If no, the apparatus branches 494 to output the angular orientation signals and then returns 496 to the beginning 460 of the main operating steps.

The apparatus can be calibrated in a straightforward manner. A convenient method is to use look-up tables ("LUTs") which can also be configured as a region of the general memory. Calibration can be conducted either at the manufacturer's factory, or by the user. Considering first the compensating angular position sensors, such as the inclinometer and compass, the apparatus is mounted with one of the three axes selected for calibration on a rotary positioning table. The table is moved through a sequence of precisely known angles (for the axis being calibrated). Both the angle and the corresponding sensor output are recorded for each of the sensors (including both inclinometer outputs).

The foregoing steps are repeated for the other two axes. Then, for each axis interpolations are taken between each successive pair of actual angles and signal outputs, to create a function $\Theta_{ind}=f(\Theta_{actual})$. A dense array of samples of the inverse of the function f is stored as a look up table for applying the inverse of the function to arrive at an actual angular orientation from the indicated angular orientation. This basically overcomes problems of non-linearities present in the angular position sensors.

The additional data stored for the other two axes is used to generate a single cross-axis sensitivity coefficient between each pair of axes.

The drift sensitive angular rate sensors are calibrated in a similar manner. The apparatus is mounted on a rotary rate table equipped with a precision angular rate sensor. The rate table is oscillated about a selected one of the three axes. The outputs from the precision reference angular rate sensor and from all three apparatus angular rate sensors are recorded. The foregoing steps are conducted for each of the remaining two axes.

Finally, parameters are fit to the recorded signals for the same axis nonlinear polynomial terms and for linear cross-axis sensitivity coefficients. These parameters are stored for use in the error compensation procedures 464 in the operating steps shown in FIG. 4C. If the nonlinearities are not easily modeled by a few parameters, the LUT approach may be used for linearizing angular rates as well.

Figure 8:
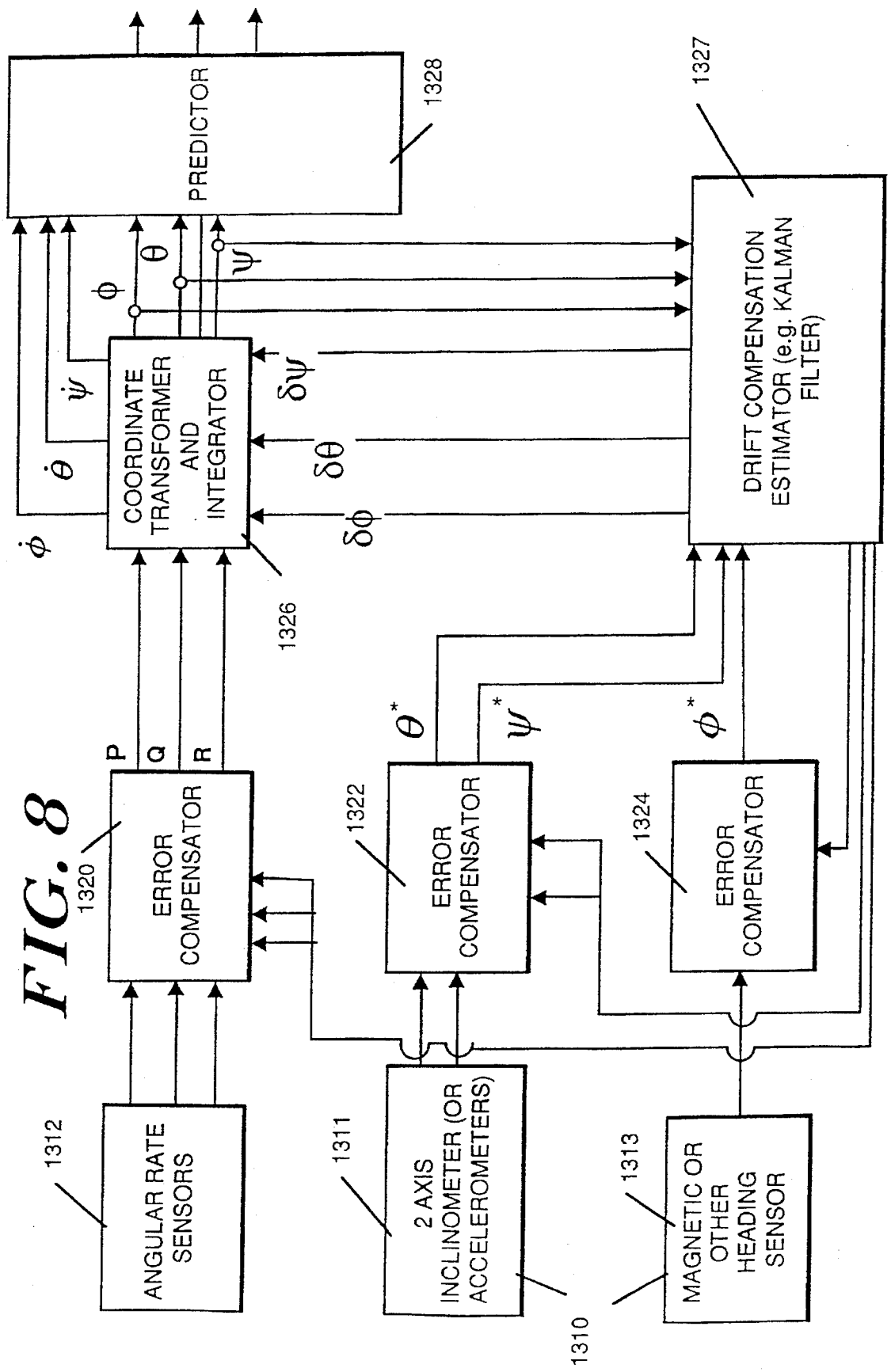
FIG. 8 is a more detailed view of a preferred embodiment of the apparatus of the invention.

The foregoing main operating steps may be further understood with reference to FIG. 8, which shows schematically in block diagram form, the functions that are performed by various components of the invention and the signals generated by each. The functions can typically be performed by hardware or software implementations. The designer will choose between the two depending upon requirements of speed, cost, size, etc.

Drift sensitive sensors 1312 generate three separate signals, which are treated at an error compensator 1320, which outputs signals that correspond to the angular rates P, Q and R, in the body coordinates. The drift compensating sensors 1310 also generate three signals, which are passed to similar error compensators 1322, 1324. In a typical embodiment, the drift compensating sensors include two types: a two axis inclinometer or two or three accelerometers 1311, which generates signals that correspond to tilt (pitch and roll) and a magnetic or other heading sensor, 1313, which generates signals that correspond to yaw. The signals output from the tilt compensating sensors, after correction, are labeled $\theta^*$ and $\psi^*$, and correspond, as explained above, to the angular orientations $\theta$ and $\psi$. The signal output from the heading compensating sensor, after correction is labeled $\phi^*$, and corresponds, as explained above, to the angular orientation $\phi$.

The three angular rate signals P, Q and R, are passed to a processor 1326, which transforms them into ground based coordinates, and also integrates them with respect to time, to arrive at the angular orientation signals $\phi$, $\theta$ and $\psi$.

If nothing were done to these orientation signals, they would drift over time, as has been discussed. These integrated signals $\phi,\theta$ and $\psi$ are provided to a drift compensation estimator 1327, which performs the steps discussed above in connection with the main operating routine of the invention. Those steps include determining whether it is an appropriate time to use the compensating sensor signals, determining the error between the drift sensitive signals and the actual angular orientation, determining the fractional amount of the error to add to the drift sensitive signals, etc. Thus, the principal output signal of the drift compensation estimator 1327 is three fractional error signals, $\delta\phi, \delta\theta$ and $\delta\psi$. These fractional error signals are provided as additional inputs to the integration module 1326, which also adds the fractional error signals to the drift sensitive signals in conjunction with the integration step (steps 470 and 476 in FIG. 4C). Thus, the output signals, $\phi,\theta$ and $\psi$ from the integration module 1326 are provided with drift compensation, and very closely approximate the actual angular orientation.

The drift compensation estimator 1327 may implement a simple compensation scheme, as discussed above (i.e., measure the difference between drift sensitive and compensating signals, provide a fraction of the difference sequentially over time until the entire difference has been added). Alternatively, a more sophisticated estimator may be used, such as a Kalman filter, which makes use of the statistical features of all of the signals. If a Kalman filter is used, it may also analyze the raw sensor signals, and then generate output signals that can be used to make the error compensators 1320, 1322, 1324, more efficient. For instance, the Kalman filter can determine that a sensor bias is changing over time.

The Kalman filter can also make judgments about whether it is an appropriate time to use the compensating signals, which judgments are more sophisticated than simply determining whether an appropriate time period has elapsed. This makes the system operate with higher accuracy in a least square error sense. Further, a Kalman filter can make use of the compensating sensor signals even during time periods when they are subject to accelerations.

A predictor 1328 may also be provided, which takes as its inputs the angular rate signals $\dot\phi,\dot\theta$ and $\dot\psi$ and the drift compensated angular orientation signals $\phi,\theta$ and $\psi$. The purpose and methods for this prediction will be discussed later, in connection with the additional embodiments of the invention.

An inertial head-tracking apparatus has many advantages over the known technologies. Since inertial measurements are not relative to any fixed equipment in the user's environment, it is theoretically possible to track the head with undiminished performance over an unlimited range or working volume. For many applications, such as architectural walk throughs, entertainment, see-through head mounted displays, and psychophysical experiments on sensorimotor integration, this is a very important feature.

A second major advantage of an inertial head-tracking apparatus is that it can be very fast. The integrated outputs of angular rate sensors (and accelerometers) are ready to be used without any delay-ridden filtering. The only other head-trackers which have essentially instantaneous response are mechanical trackers, which suffer from very strict range limitations. Speed, or responsiveness, is a very important aspect of tracker performance. Excessive delay added into the head-motion-to-visual-feedback loop destroys the illusion of presence and can cause simulator sickness.

A third advantage of inertial head tracking apparatus is that they are free of the interference and line-of-sight problems that plague all known trackers. A pure inertial system does not send or receive any signals from its environment and therefore its performance will not be affected by any kind of electromagnetic interference or occlusions of acoustic or optical sources, or the operation of any other tracking systems in its vicinity. The only external field that a pure inertial tracking apparatus senses is gravity. Gravitational interference is not a problem because the movement of mass in the vicinity of the tracker produces gravitational variations so much smaller than the Earth's gravitational field that they will have no effect on the accuracy of the apparatus. (It should be noted that if a compass is used to compensate for drift with the yaw sensor, the apparatus is not a "pure" inertial apparatus.)

Yet another advantage is a different design approach to the head-tracking problem, facilitated by inertial techniques. Acoustic and inside-out optical trackers only measure position. Orientation is then computed from the positions of three fixed points on the head. Therefore, the angular resolution is limited by the uncertainty in the position measurements as well as the distance between the three fixed points on the head. With 100 mm spacing between the fixed points, a positional jitter of ±1.0 mm causes an orientational jitter of up to ±1.1°. Inertial systems, on the other hand, measure the angular orientation freedoms directly, so that it is possible to make a self-contained orientation-tracking module, whose performance is in no way affected by the quality of the position-measuring subsystem, or even the lack thereof. The existence of such independent orientation and position subsystems make possible a more modular approach to virtual environment system design. The designer is able to select an orientation-tracker and an independent position-tracker with appropriate specifications for the application. In an extreme case, such as a virtual environment in which the user navigates by making hand gestures and not by walking about, it is perfectly reasonable to use no position-tracker at all.

Test Results

Figure 5A:
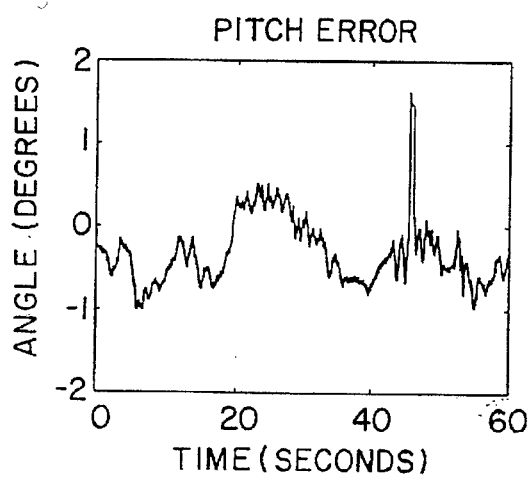
FIG. 5A is a graphical representation of the error in the pitch angle as determined by a preferred embodiment of the apparatus of the invention.
Figure 5B:
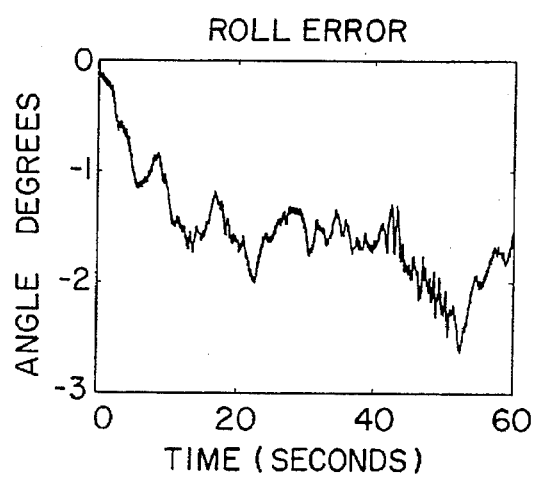
FIG. 5B is a graphical representation of the error in the roll angle as determined by a preferred embodiment of the apparatus of the invention.

Tests have been conducted to show the accuracy of the Gyrochip embodiment discussed above, with respect to pitch and roll (combined, known as tilt). The apparatus was fixed to an angular reference jig, with either the pitch or roll axis aligned with the axis of rotation, and then the outputs of the tracking apparatus of the invention and the angular reference jig were recorded for one minute, with a sampling rate of 48.55 Hz. During the minute, the tracking apparatus of the invention was rotated randomly by hand to simulate the type of motions that would be encountered by a head-tracker in actual use. The graphs shown in FIG. 5A and FIG. 5B show the error for the pitch and the roll respectively computed by subtracting the signal generated by the measurement jig from the signal generated by the invention.

Resolution and Noise

Figure 6A:
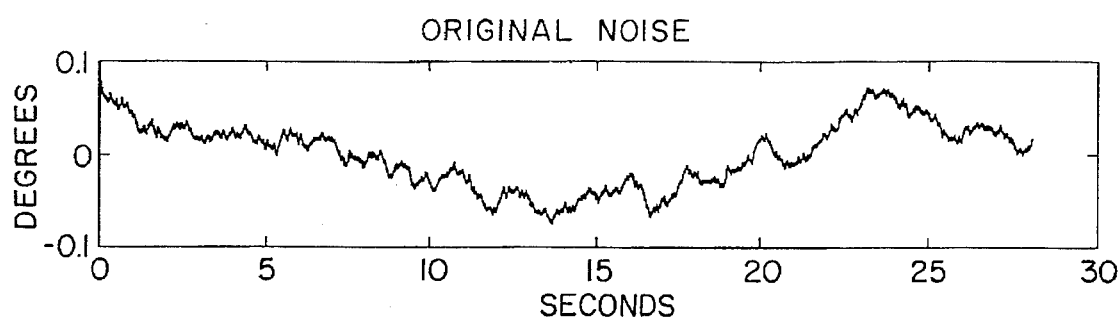
FIG. 6A is a graphical representation of the noise signal generated by an embodiment of the invention attached to a stationary body.

FIG. 6A shows a magnified view of the noise sample that was obtained from the stationary tracker for the purpose of evaluating the resolution. This data record comprises 4096 samples of the yaw output taken at a sampling rate of 145.65 Hz. Most of the noise energy is concentrated below 1 Hz, which explains why the noise trace meanders more slowly than is typical of white or pink noise. "Noise" is used here to mean a measure of the fast fluctuations in the output of the head-tracker that would lead to distracting scene jitter. Since scene rotations slower than 0.05°/s are not even perceptible, let alone distracting, the very slow fluctuation is not considered to be noise. Noise is used here to mean the signal that remains after subtracting from the raw noise signal any low-frequency component that varies more slowly than 0.05°/s.

Figure 6B:
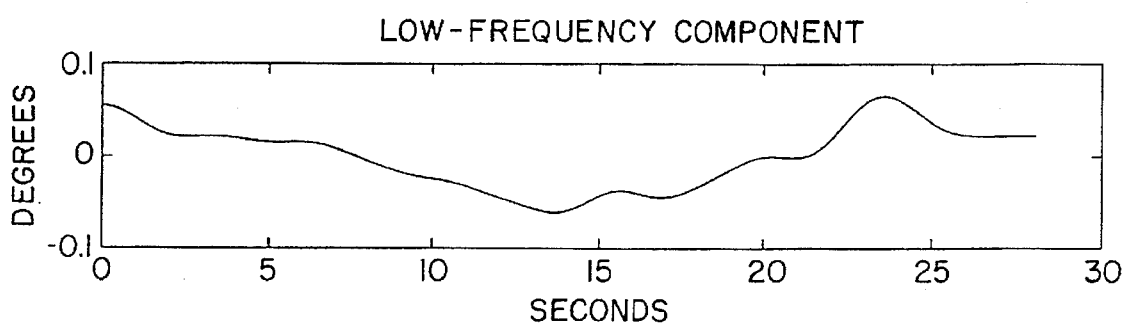
FIG. 6B is a graphical representation of the low frequency component of the noise signal shown in FIG. 6A.
Figure 6C:
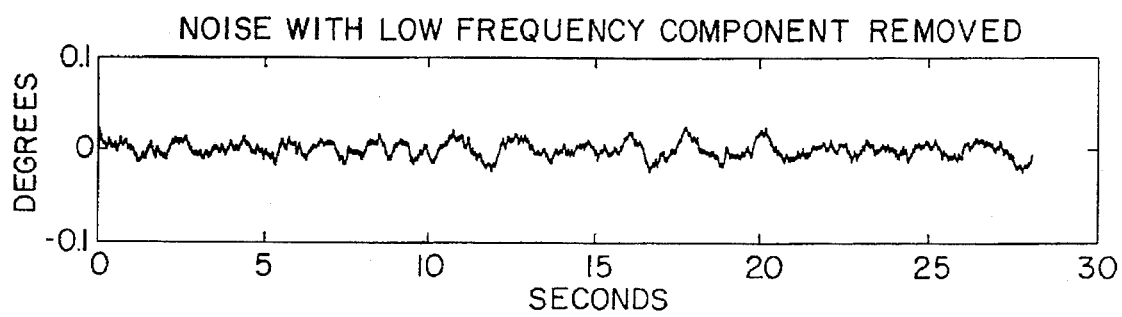
FIG. 6C is a graphical representation of the noise signal shown in FIG. 6A, with the low frequency component removed.

Low pass filtering the noise with a cutoff frequency of 0.35 Hz extracts a low-frequency component whose derivative has maxima just under 0.05°/s, which is shown in FIG. 6B. FIG. 6C shows the high pass version of the noise obtained by subtracting the low pass version from the original. The RMS amplitude of this "de-drifted" noise, 0.0082°, will be taken as the resolution of the embodiment of the head-tracking apparatus of the invention described above. This is comparable to the resolution of a mechanical tracker with 16-bit conversion.

Dynamic Response

Excessive head-tracker delay has a profoundly destructive effect on virtual environment realism, and can even induce nausea and vomiting. The need for a fast head-tracker is one of the major motivations for the present invention. Therefore, the dynamic performance of the embodiment was tested thoroughly.

The pitch, roll and yaw system functions are basically the same. Therefore, this evaluation focuses entirely on determining the system function for pitch. The testing apparatus and software available makes it easy to simultaneously record the actual pitch angle, v(t), and the pitch output reported by the tracking apparatus of the invention, w(t), for the same time period $0 \leq t \leq T$. The head-tracking apparatus on a reference jig is hand-shaken as vigorously as possible at a variety of frequencies for about 30 seconds, while the excitation angle and tracker output are simultaneously recorded with 145 Hz sampling rate. The system function is then determined as $$H(f) = \frac{W(f)}{V(f)}$$

where V(f) and W(f) are the discrete-time Fourier transforms of v(t) and w(t).

Figure 7A:
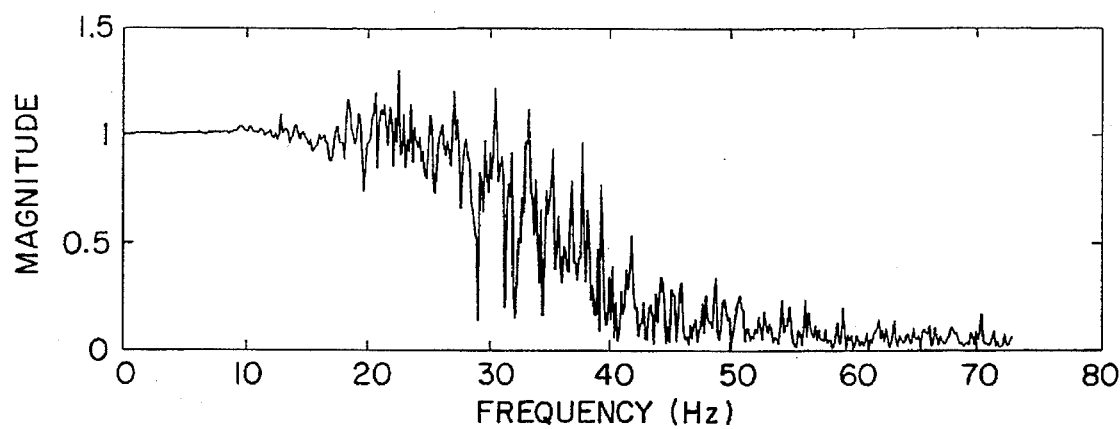
FIG. 7A is a graphical representation of the magnitude of the transfer function for the pitch axis of a preferred embodiment of the apparatus of the invention.

FIG. 7A shows the system function obtained in the manner described above. Up to about 10 or 15 Hz, the magnitude is 1 and the phase is 0, as desired. At higher frequencies both the magnitude and phase become erratic. This is because the excitation contains insufficient energy at high frequencies; it does not indicate that the bandwidth of the tracker is only 15 Hz. Given that the bandwidth of the GyroChip angular rate sensor is 100 Hz, it is expected that the system function of the head tracking apparatus of the invention would be flat, out to the Nyquist frequency of 70 Hz, if it could be measured that far. It is not, however, important to demonstrate flat response all the way to 70 Hz. It has been demonstrated that the bandwidth of human volitional movement is on the order of 10 Hz. Both the Polhemus Isotrack brand magnetic tracker and Logitech brand 6-D ultrasonic mouse show significant gain roll off below 3 Hz.

Figure 7B:
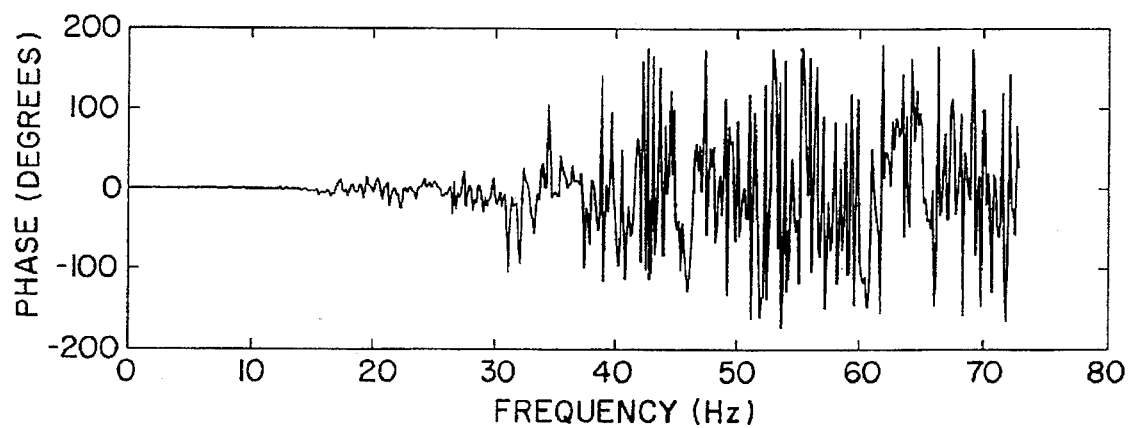
FIG. 7B is a graphical representation of the phase of the transfer function for the pitch axis of a preferred embodiment of the apparatus of the invention.

Having determined from the system function magnitude that the tracker bandwidth is more than adequate for tracking human head motion, it is also possible to obtain an empirical measure of the system lag by looking at the phase response in FIG. 7B. A least squares linear regression to the phase from 0 to 10 Hz has a slope of 0.037°/Hz, which corresponds to a lag of 0.10 ms. The design goals for dynamic performance have clearly been achieved.

General Conclusions

Table 1 summarizes the results from the evaluation and compares them to desired specifications.

TABLE 1

| SPECIFICATION | DESIRED | INVENTION |
|---|---|---|
| ANGULAR RANGE | yaw: ±180° | yaw: ±180° |
|  | pitch: +50°, −70° | pitch: ±90 |
|  | roll: ±35° | roll: ±90° |
| POSITIONAL RANGE | room size | unlimited |
| ANGULAR VELOCITY | ±1000°/sec | ±1000°/sec |
| ANGULAR ACCELERATION | ±6000°/sec² | >6000°/sec² |
| ANGULAR ACCURACY | opaque HMD: yaw: none pitch & roll: 15° max drift rate: 3°/min. see-through HMD: 0.009 | yaw: ~3°/min. drift pitch & roll: 1° |
| ANGULAR RESOLUTION | opaque HMD: 0.03° see-through HMD: 0.009° | 0.0082° RMS |
| Bandwidth | 20 Hz | tested to 15 Hz |
| Latency | 1 ms | 0.1 ms |

Figure 10:
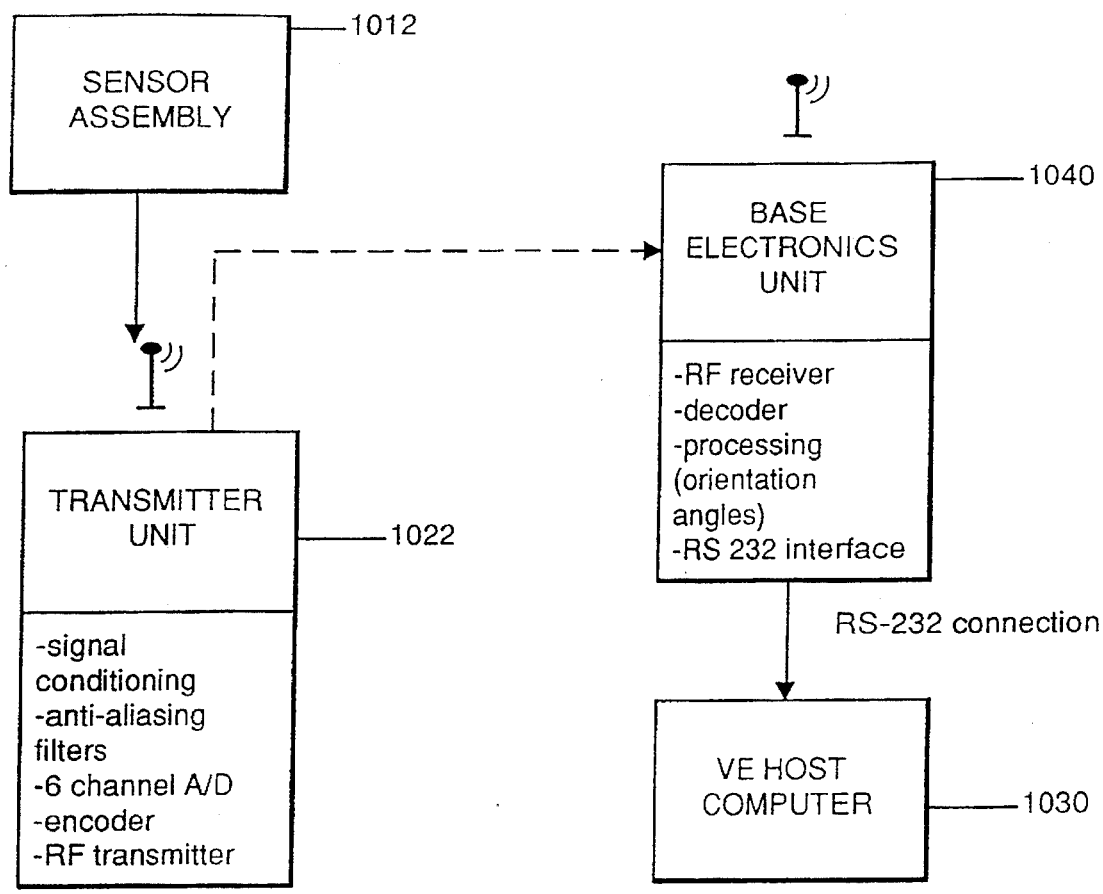
FIG. 10 is a block diagram illustration of basic components of a wireless embodiment of the apparatus of the invention.

The results show that the Gyrochip embodiment of the inertial orientation tracking apparatus described above successfully meets most of the head-tracking orientation needs that have not been met by mechanical, acoustic, magnetic and optical systems. The range of the inertial tracker apparatus of the invention is potentially larger than any other head-tracker yet devised. All possible orientations are tracked, although for drift correction to occur the user must occasionally pause. Use of a Kalman filter minimizes the frequency and duration of such required pauses and may even eliminate the need. Positional range is also unrestricted. By using long enough wires, a user may wander freely throughout a room of any size. If the application requires the user to travel even greater distances, such as throughout a large building or outdoors, or around obstructions, the signal link 316 (FIG. 3) can be implemented by wireless telemetry, such as radio transmission, as shown in FIG. 10. The inertial orientation-tracker achieves unlimited range, however, this is in the absence of tracking position. If all six degrees of freedom are to be tracked, in order to provide unlimited range, a position tracking system that also has unlimited range must also be used.

Another extremely important advantage of inertial tracking, which is successfully demonstrated by the apparatus described above, is speed. The lag is certainly no greater than 1 ms, as an update rate of 1 kHz was achieved. According to an analysis of the phase response, the effective lag is only 0.1 ms. The bandwidth is also more than adequate for human motion-tracking applications.

The noise and resolution results are also favorable. Because the inertial tracker integrates the sensor data, the resolution of the outputs is much finer than the resolution of the A/D converters used to sample the sensor data. Even with 11-bit effective conversion precision, the high frequency noise in the outputs is only ~0.008° RMS or 0.05° peak-to-peak. By comparison, the orientation jitter shown for a Polhemus Isotrack brand magnetic tracker, is on the order of 0.3° peak-to-peak.

Although the yaw drift rates of about 100°–300°/hr achieved by the embodiment of the invention discussed above are perfectly tolerable for opaque VE applications with no interaction with the real environment, the drift accumulated after several minutes would be enough to make contact with the real environment confusing. Using the magnetic compass system for yaw drift compensation renders applications requiring registration of the real and virtual worlds possible.

It is always desirable to reduce the uncompensated drift rate, because the product of the drift rate and the interval between corrections determines the bound on the system accuracy. As the drift rates intrinsic to the Systron-Donner brand angular rate sensors used for a prototype design are about 30 times smaller than those achieved, it should be possible to make significant reductions by replacing the 12-bit A/D converters with 16-bit converters, adding anti-aliasing filters, and improving the software to reduce numerical errors.

Additional Preferred Embodiments

The invention has been described above with respect to a preferred embodiment that uses angular rate sensors for the drift sensitive sensors and a two axis pendulum and a fluxgate magnetometer for the drift compensating sensors. These components are not required. What is required is a relatively high bandwidth set of sensors, to generate a signal that corresponds to the angular orientation, but which signal may deteriorate over time. The deterioration may be due to bias, noise, drift, etc. Additionally, the apparatus has a means for correcting for the deterioration or drift. One means, shown above, is to use additional compensating sensors mounted generally near the drift sensitive sensors. The additional sensors do not generate orientation information in such a way that they can be used alone by the apparatus without any other sort of sensor information. However, they are not subject to drift. Thus, they can be used to correct the substantially continuously generated, but drifting signal. For instance, the compensating sensors may take a longer period of time to settle to a fixed output. Such is the case with a fluid inclinometer. Another type of compensating sensor disability is sensitivity to another influence, such as acceleration, which is not sought to be measured.

The drift sensitive sensors discussed above are solid state angular rate sensors. The coriolis forces generated in a vibrating quartz tuning fork when it rotates about its axis cause out-of-plane vibrations proportional to the velocity of rotation. The out of plane vibrations give rise to an A.C. voltage due to the piezoelectric effect. Any other angular rate sensor that is small and light enough for mounting on the body member in question is contemplated to be used with the invention.

Another suitable candidate for the drift sensitive sensor is a fiber-optic gyroscope ("FOG") such as is sold by Litton Guidance & Control of Woodland Hills, Calif., under the trade designation LN-200. Such devices send a light signal in two directions around a spool of fiber-optic material and detect the phase difference when the light signal meets itself. These devices can achieve ±1000°/s range, 0.03°/√hr random drift. They are, however, rather large and expensive at this writing. An integrated circuit version of the FOG, called the Micro-Optical gyro ("MOG") is expected to be available in the near future.

Another suitable drift sensitive sensor is a rate gyroscope, using a spinning rotor mounted on a gimbal. The gimbal does not rotate freely. When the housing of the gimbal and rotor changes direction, the rotor is forced by the stiff gimbal to change orientation with it. To change the spin axis requires a torque proportional to the rate of change and this torque can be measured on the axis of the gimbal and used as a reading of angular velocity. A suitable rate gyroscope is sold by Litton Guidance & Control, identified above, under trade designation G2000, having ±400°/s range, 0.1°/hr drift, and a size (per axis) of on the order of 0.75 in. diameter×0.75 in (1.9 cm×1.9 cm) and 0.8 oz (0.226 kg.) These devices are also rather expensive, but would operate well according to the principals discussed above.

Another type of drift sensitive sensor is a spin gyroscope that generates a position signal rather than a rate signal. A spin gyroscope consists of a spinning wheel mounted on a three axis gimbal designed to be as frictionless as possible. When the outer housing rotates, the gimbals swivel to allow the wheel to continue spinning on the same axis. Angular encoders measure the rotations of the gimbals, which correspond to the orientation of the housing with respect to the spin axis. As rotations about the spin axis are not measured, one spin gyroscope can measure at most two orientational degrees of freedom. The usual arrangement involves two spin gyroscopes, one for measuring pitch and roll (called a vertical gyroscope) and one for measuring yaw (called a directional gyroscope). To make sure that the spin axis is vertical for a vertical gyroscope and horizontal for a directional gyroscope, the gimbals may be weighted so that they hang in the correct reference orientation before spinning up the rotor. This is called a pendulum-leveled gyroscope. For the vertical gyroscope the pendulum also prevents unbounded drift by gradually restoring the axis to vertical through a sequence of damped precessions. The disadvantage of this approach is that linear accelerations generate unbalanced torques on the gimbals, which cause precession. To avoid this, some navigational gyroscopes are instead leveled by active electromagnetic torquers. A suitable spin position gyroscope is sold by Gyration, Inc. of Saratoga Calif., under trade designation GyroEngine, having ±80° range, 5°–10°/min. drift, and a size for two axes of on the order of 1.75 in.×1.25 in (4.5 cm×3.2 cm) and 1.2 oz (0.034 kg). (Two gyros are needed.) The angular rate sensors may also constitute a silicon micro-machined sensor or a magnetohydrodynamic ("MHD") angular rate sensor. Magneto-optical gyros may also be used.

Turning now to candidates for the sensors for compensating for drift, as mentioned above, a preferred apparatus uses an inclinometer and a compass. Other configurations include using two or three accelerometers for registering tilt and an optical or RF sensor for registering heading. The latter two are not, however, impervious to interference.

A suitable inclinometer is sold by Fredericks Co. of Huntington Valley, Pa., under the trade designation 0717, having a ±70° non-linear range, 0.03° repeatability, and a physical size of 0.6 in×0.3 in diameter (1.52 cm×0.76 cm dia.) for a two axis sensor. Because the output is highly non-linear, it must be converted to actual angles using a look up table (LUT) as discussed above. If the table contains enough entries, the absolute accuracy will be totally determined by the repeatability. The repeatability of 0.03° is only a factor of 3.3 greater than the minimum perceptible misalignment angle in the most stringent applications. This is adequate for many applications. The inclinometer has a settling time of 245 ms.

Detecting the direction of heading is more difficult than detecting tilt. Gravity points down very consistently, and is barely influenced even by large mountains. By contrast, the earth's magnetic field has a dip which depends on latitude, and is affected significantly by power lines, electrical equipment and nearby large amounts of iron or steel. Thus, one must take into account the complex shape of the magnetic field in a typical user's environment. The latitudinal dips can be dealt with by initial calibration, as long as the user's range does not transcend great distances in latitude.

A product is available from KVH Industries, of Middletown R.I., under trade designation C100 Compass Engine, which combines a fluxgate compass with a microprocessor to perform automatic compensation for deviation caused by iron in the installation equipment. This requires an initial compensation procedure to store the mapping pattern of the installation equipment and yields absolute accuracies of 0.5°. However, it only compensates for iron that moves with the sensor so it will not help with irregularities in the external field.

In a preferred embodiment, the sensors are as small and light as cost and performance allow. All of the electronics is integrated on a printed circuit card that can be housed in an expansion slot of the computer, so that the entire head-tracker system consists of a programmed computer and a small sensor block with one long thin cable that plugs into the back of the computer.

While the present implementation uses a programmed general purpose computer, if the cost of the system warrants, a dedicated processor can be used that implements the signal processing modules discussed above, principally, the angular conversion from body to ground related axes, the integration of angular rates over time, the still-time monitoring, the correction of the drift sensitive sensor signal with the drift compensating sensor signal, etc.

To improve user mobility, a wireless link, such as an RF channel link, can be used for the signal link 316 as shown in FIG. 3. The wireless link can be interposed anywhere in the signal path, at the discretion of the designer, depending on the weight and computational capacities of different portions of the apparatus. One such embodiment is shown schematically with reference to FIG. 10. The sensor assembly 1012 is mounted on the head, and is connected through a short (1 m) cable to a transmitting unit 1022 carried in a more convenient location, such as on the belt, in a pocket or in a backpack. The transmitter may include signal conditioning circuitry, anti-aliasing filters, A/D converter, an encoder and an RF transmitter. A base electronics unit 1040 includes an RF receiver, a decoder, apparatus for computing the orientation angles, such as a processor and suitable memory, as shown in FIG. 3, and an interface for connection to a virtual environment generating apparatus 1030, such as another computer. A convenient interface is an, RS-232 interface, such as is used for computer serial communications.

Rather than using a wireless unit, the sensor assembly 1012 can be connected to a table top unit through a long (3 m) thin multiwire cable. The table top unit includes the signal conditioning electronics, anti-aliasing filters, A/D converter, processor, and RS-232 interface.

The inertial head tracking apparatus of the invention can also be used to improve the overall delay that a virtual environment system experiences in rendering the environment in response to a change in head orientation. Delays from 5–100 ms have been proposed as the maximum tolerable delay between head-motion and response in a virtual environment. Presently, it is difficult to achieve a lag of less than 30 ms for the rendering aspect of a virtual environment system alone. Thus, it is desirable to minimize the delay between head motion and when the orientation tracking apparatus generates a signal that corresponds to that head motion.

One way to reduce the overall time is to use a motion prediction technique, where the motion of the head is predicted, and the prediction is used by the rendering apparatus to begin its time consuming rendering even before the head has moved. Since the inertial head-tracker is already equipped with angular rate sensors and, for some embodiment, linear accelerometers, these signals can be made available to an external or internal orientation prediction apparatus at no additional hardware cost. This is a significant advantage over other tracking technologies. The prediction apparatus is most accurate when still or at constant velocity. The largest overshoots/errors occur during sudden changes in velocity or acceleration.

Figure 11:
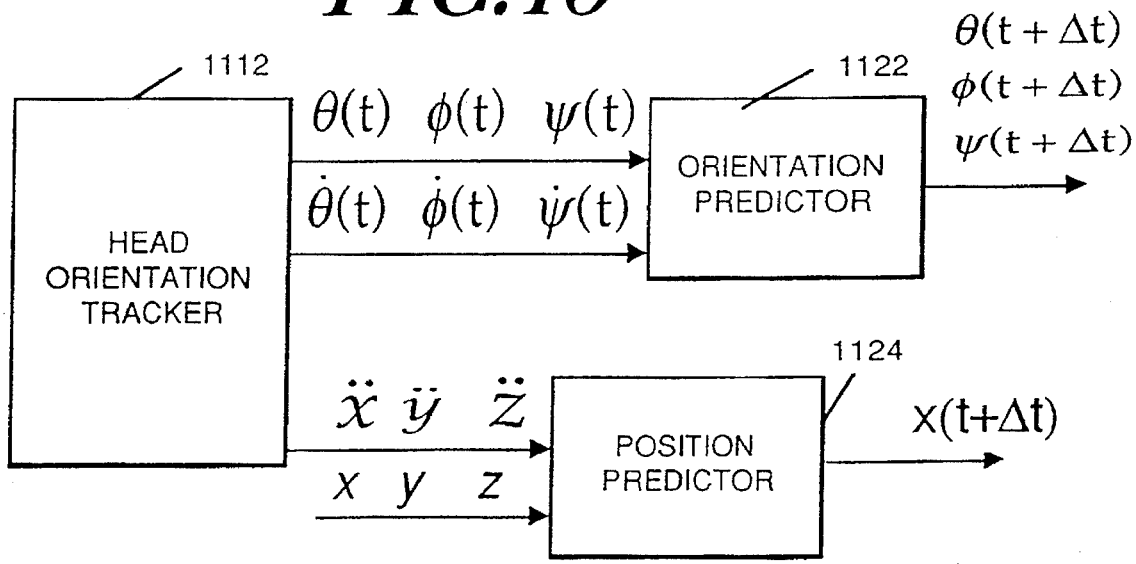
FIG. 11 is a block diagram illustration of basic components of an embodiment of the invention using orientation and position prediction modules.
Figure 12:
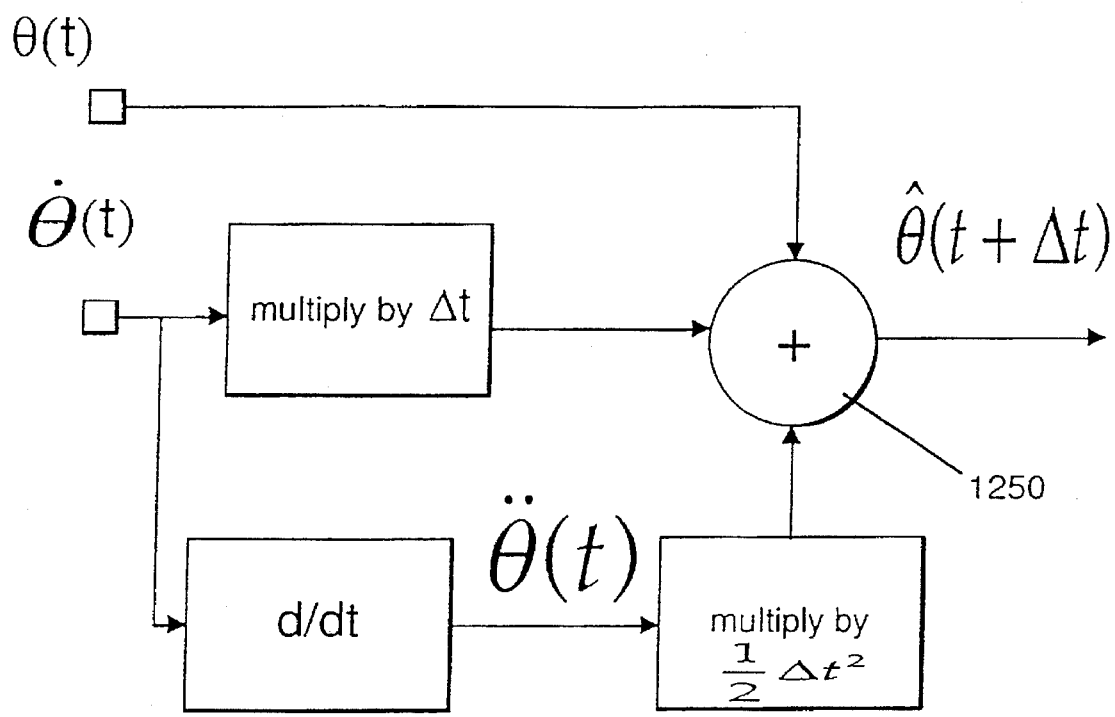
FIG. 12 is a block diagram illustration of an orientation predictor.

Implementation of such a prediction device is shown schematically in block diagram form in FIG. 11. The head tracking apparatus 1112 generates angular orientation outputs $\theta, \phi$ and $\psi$ as discussed above. The outputs (after signal conditioning and coordinate conversion) from the angular rate sensors are the derivatives of these values, i.e., $\dot\theta$, $\dot\phi$ and $\dot\psi$. Signals representing all of these values at time t are available using the embodiment discussed. An orientation predictor 1122 takes these signals, and generates a prediction for these signals at time t+Δt. A rudimentary orientation predictor for a single angle, e.g. $\theta$ is shown with reference to FIG. 12. An adder 1250 adds together the signal for $\theta$ with the product of the signal representing $\dot\theta$ and the time increment Δt. This sum is further added to the product of the derivative of the angular rate, $\ddot\theta$ and ½ the square of the time increment Δt. The output signal is a reasonable prediction for what the value of the angular orientation $\theta$ will be at future time t+Δt.

The same can be done for the other angular orientations $\phi$ and $\psi$. If accelerometers are used, the linear position of the head can also be predicted in the same manner, using the signals output from the accelerometers, as shown in FIG. 11. The position predictor 1124 is basically the same, substituting a position signal for an angular orientation signal. It is also possible to use a sophisticated Kalman filter predictor as the predictor 1122 or 1124, which uses statistics about human head motion to further refine the prediction apparatus. Motion prediction is discussed in more detail in M. Friedmann, T. Starner, and Pentland A., "Synchronization in virtual realities," *Presence*, 1(1): 139–144, Winter 1992; Jiandong Liang, Chris Shaw and Mark Green, "On temporal-spatial realism in the virtual reality environment, *Fourth Annual Symposium on User Interface Software and Technology*, pp. 19–25, November 1991; and Uwe H. List, "Nonlinear prediction of head movements for helmet-mounted displays," AFHRL Technical Paper 83–45, Air Force Human Resources Laboratory, Operations Training Division, Williams Air Force, 1983, all three of which articles are incorporated herein by reference.

It is also useful to use a Kalman filter to combine the outputs from the two sets of sensors in the most appropriate manner. In general, a Kalman filter uses statistical and probabilistic information about the signal output by the two sets of sensors to make decisions about how much to weight the signals provided by one set of sensors, relative to the other. For instance, if the Kalman filter decides that there is a high probability that the compensating sensor signal accurately reflects the angular orientation, that sensor signal is weighted more heavily than the signal output by the drift sensitive sensors. The Kalman filter can also be used to analyze the bias of the sensors over time, to determine whether the bias is changing or not. If the bias is changing, an accommodation can be made.

A schematic diagram showing implementation of a head tracker using a Kalman filter estimator is shown in FIG. 8. Drift sensitive sensors generate three signals, which are passed to an error compensation module 1320, to correct for temperature sensitivity, bias, nonlinearity, and axis misalignment, etc. The output from the error compensation module is provided to a module 1326 that performs coordinate transformation and integration, and outputs the Euler angles $\theta$, $\phi$ and $\psi$. Similarly, the compensating sensors 1310, consisting of, for instance a two axis inclinometer 1310*i* and a magnetic or other heading sensor 1310*m*, each output angular position signals, which are also corrected by respective error compensation modules 1322 and 1324. The outputs of the drift compensating sensors (error compensated) $\theta^*$, $\phi^*$ and $\psi^*$, are provided to the Kalman filter 1327. Also provided to the Kalman filter are the outputs $\theta$, $\phi$ and $\psi$ from the integration module 1326. The Kalman filter monitors these six signals over time, and, based on its configuration, assesses how to combine them to minimize the overall system error with respect to the orientation angles $\theta$, $\phi$ and $\psi$. After determining the desired angles, the Kalman filter computes incremental orientation correction signals $\delta\theta$, $\delta\phi$ and $\delta\psi$, which correction signals are provided back to the coordinate transformation and integration module 1326, which combines the error signals with the input signals in an appropriate manner.

The Kalman filter is also capable of analyzing the outputs from all of the sensors, either raw or error compensated, and determining the evolution over time of the sensors' biases and other noise or non-signal signal components. The results of this determination can be used by the error compensation modules 1324, 1322 and 1320 to enhance their functions. A prediction module 1328 is also shown. It may be implemented as described above, or it can also be implemented by the Kalman filter. The Kalman filter can even encompass the transformation and integration module 1326. However, such a use has high computation requirements.

The inertial head or body member tracking apparatus can be used in a number of applications. The head tracker can be used with opaque virtual environments, where the entire environment is presented to a display, typically a head mounted display, and the environment changes in response to, among other things, the user's body motions. For instance, the environment changes to reflect a point of view that the user adopts. The tracker can also be used in a see-through environment, where the user has visual access to the real environment, but in addition, a virtual environment is superimposed on the real environment, for instance using half silvered mirrors. In either case, a haptic interface can also be provided, where the user experiences tactile sensations generated by a virtual environment controlled by a computer. The computer may be the same computer that makes up part of the head tracking apparatus, or it may be a separate computer. The visual rendering can be through a head mounted display, as shown in FIG. 2.

Figure 9:
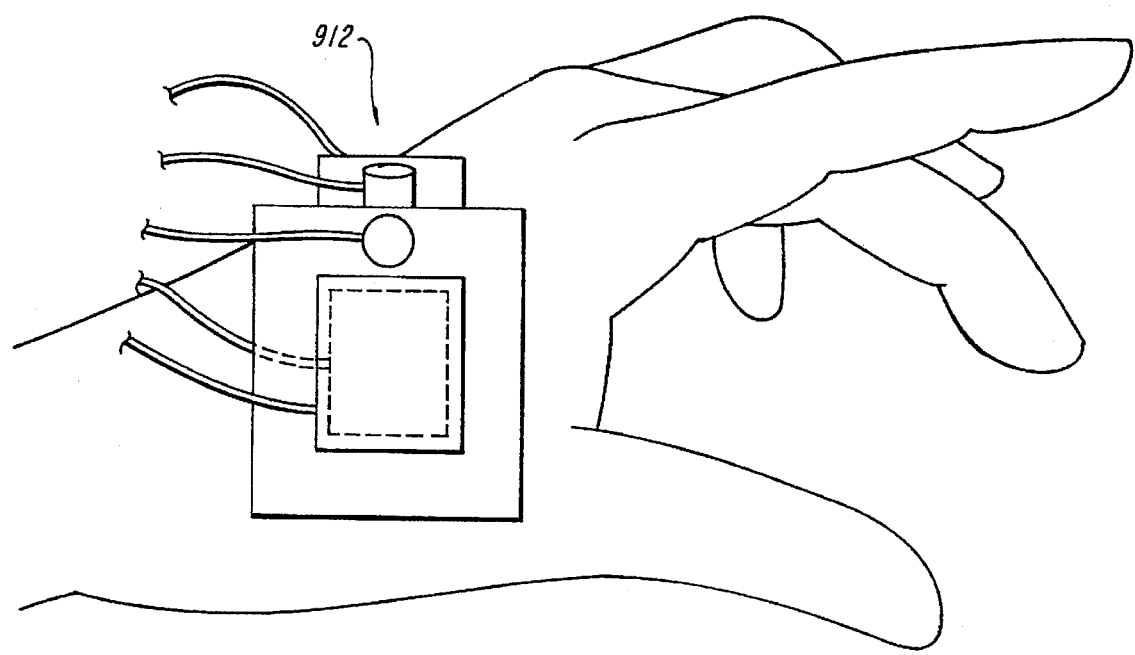
FIG. 9 is a schematic illustration of an embodiment of the apparatus of the invention mounted upon a user's hand.

In a sense, in a virtual environment, the user's motions act as input commands to the computer that operates the virtual environment. The user's motions can also act as input commands for any type of machine that must be controlled. An operator wearing a tracking apparatus 912 of the invention on a hand, as shown schematically in FIG. 9, can control a robot arm to obtain the same orientation as the user's hand. A user whose hands or feet are occupied with other tasks, or incapacitated through injury, can use a tracking apparatus of the invention mounted upon the head to control machinery that is more conventionally controlled by hand or foot. Such a device can be used to monitor the condition of persons who are prone to unexpected seizures or fainting spells, who seek to live independently, but require aid if stricken.

The foregoing discussion should be understood as illustrative and should not be considered to be limiting in any sense. While this invention has been particularly shown and described with references to preferred embodiments thereof, it will be understood by those skilled in the art that various changes in form and details may be made therein without departing from the spirit and scope of the invention as defined by the claims.

Having described the invention, what is claimed is:

1. An apparatus to be attached to a body having a size between the sizes of a human finger and a human torso, said body having an orientation, relative to an external reference frame, said apparatus generating an orientation signal that corresponds to at least two degrees of freedom of said orientation of said body, said apparatus comprising:

a. a self contained sensor that generates first sensor signals that correspond to $x^{th}$ order integrals of rotational accelerations of said body about at least two axes of said body, x being selected from the group consisting of 0, 1 and 2 and said first sensor signals being impervious to any interference from electromagnetic, acoustic, optical and mechanical sources;

b. a mechanism for mounting said sensor to said body; and c. coupled to said sensor, a signal processor that generates an orientation signal that corresponds to said at least two degrees of freedom of said orientation of said body.

2. The apparatus of claim 1, said sensor comprising angular rate sensors and the order x being equal to 1 and said first sensor signals corresponding to rotational rates of said body.

3. The apparatus of claim 1, said sensor comprising gyroscopes and the order x being equal to 2 and said first sensor signals corresponding to said at least two degrees of freedom of said orientation of said body.

4. The apparatus of claim 2, said angular rate sensors comprising three angular rate sensors arranged to span three space.

5. The apparatus of claim 4, said signal processor comprising an integrator that integrates said rotational rate signals with respect to time and generates a signal that corresponds to orientation.

6. The apparatus of claim 3, said gyroscopes being arranged to comprise one vertical gyroscope and one directional gyroscope.

7. The apparatus of claim 5, further comprising a sensor error compensator, coupled to said angular rate sensors and said integrator, that compensates for errors such as bias and non-linearity in said rotational rate signals that may arise over time.

8. The apparatus of claim 5, further comprising a drift compensator, coupled to said angular rate sensors and said integrator, that compensates for any drift over time in said orientation signal.

9. The apparatus of claim 8, said drift compensator comprising at least one gravitational tilt sensor.

10. The apparatus of claim 8, said drift compensator comprising at least one magnetic field sensor.

11. The apparatus of claim 10, said magnetic field sensor comprising a compass.

12. The apparatus of claim 9, said drift compensator further comprising at least one magnetic field sensor.

13. The apparatus of claim 9, said gravitational tilt sensor comprising a two axis fluid inclinometer.

14. The apparatus of claim 4, said angular rate sensors comprising a vibrating piezoelectric apparatus.

15. The apparatus of claim 5, further comprising an orientation predictor, coupled to said integrator and to said angular rate sensors.

16. The apparatus of claim 2, said first sensor weighing less than 300 grams.

17. The apparatus of claim 2, said mounting means comprising a human head mount.

18. The apparatus of claim 2, said mounting means comprising a human hand mount.

19. The apparatus of claim 8, said drift compensator comprising a verifier that periodically measures said orientation of said body by a means different from using said rotational rate signal and generates an orientation drift compensation signal based on results of said verification measurement to reduce the effect of drift.

20. The apparatus of claim 19, said verifier comprising means for relying upon characteristic features of human motion.

21. The apparatus of claim 20, said means for relying upon characteristic features of human motion comprising an at rest sensor that identifies any occurrence of periods exceeding a predetermined duration when the body is substantially at rest relative to said reference frame.

22. The apparatus of claim 21, said at rest sensor comprising:
   a. a timer;
   b. a signal generator that generates signals that correspond to;
      i. nongravitational acceleration and;
      ii. rotation of the body;
   c. means for storing and comparing said nongravitational acceleration and rotation signals at several points over time; and
   d. a signal generator that generates an at rest signal if said nongravitational acceleration and rotation signals are both constant over a preselected time period.

23. The apparatus of claim 2, further comprising means for coupling said orientation signal to a receiver that is spaced away from said self contained sensor.

24. The apparatus of claim 23, said coupling means comprising a wireless coupling means.

25. The apparatus of claim 2, said signal processor being located spaced away from said self contained sensor, further comprising wireless means for coupling said self contained sensor to said signal processor.

26. The apparatus of claim 2, said body also having a position relative to said external reference frame, further comprising a position sensor that determines said position of said body.

27. The apparatus of claim 2, said angular rate sensors comprising spinning wheel rate gyros.

28. The apparatus of claim 4, said three angular rate sensors being selected from the group consisting of a silicon micro machined sensor assembly, a magneto-hydrodynamic device and a micro-optical gyroscope assembly.

29. The apparatus of claim 19, said drift compensator comprising a Kalman filter.

30. The apparatus of claim 9, said gravitational tilt sensor comprising at least 2 accelerometers.

31. An apparatus to be attached to a body having a size between the sizes of a human finger and a human torso, said body having an orientation, relative to a reference frame, said apparatus generating an orientation signal that corresponds to at least two degrees of freedom of orientation of said body, said apparatus comprising:
   a. a self contained sensor that generates a rotational rate signal that corresponds to at least two degrees of freedom of rotational rate of said body and, which signal is impervious to interference from electromagnetic, acoustic, optical and mechanical sources;
   b. a mounting mechanism for mounting said self contained sensor to said body; and
   c. coupled with said self contained sensor, an integrator that integrates said rotational rate signal over time to generate said orientation signal.

32. The apparatus of claim 31, further comprising, coupled with said mounting mechanism, a gravity-referenced tilt sensor that generates a tilt orientation signal that corresponds to two degrees of freedom of said orientation of said body.

33. The apparatus of claim 32, further comprising, coupled with said mounting mechanism, a magnetic field sensor that generates a signal that corresponds to a third degree of freedom of orientation of said body.

34. The apparatus of claim 33, further comprising means for substituting said tilt orientation signal and said signal that corresponds to a third degree of freedom for said orientation signal generated by said integrator, at selected times.

35. The apparatus of claim 34, further comprising a verifier that determines the time when said body is at rest relative to said reference frame, and further comprising a processor that determines the occurrence of said selected times, based on said at rest time.

36. An apparatus to be attached to a body having a size between the sizes of a human finger and a human torso, said body having an orientation, relative to a reference frame, said apparatus generating an orientation signal that corresponds to at least two degrees of freedom of said orientation of said body, said apparatus comprising:
   a. a self contained first sensor that generates a drift sensitive orientation signal that corresponds to said at least two degrees of freedom of orientation of said body and is impervious to interference from electromagnetic, acoustic, optical and mechanical sources and is subject to drift over time;

b. a second sensor that generates a drift compensating orientation signal that corresponds to said at least two degrees of freedom of orientation of said body and is relatively impervious to drift over time;

c. a mounting mechanism for mounting said first sensor and said second sensor to said body; and d. coupled to said first sensor and said second sensor, a signal corrector that generates a corrected orientation signal based on said drift sensitive and drift compensating orientation signals.

37. The apparatus of claim 36, said signal corrector comprising means to take into account characteristic features of human motion.

38. The apparatus of claim 37, said means to take into account characteristic features of human motion comprising means to determine times when said body has been at rest for more than a predetermined period of time.

39. The apparatus of claim 38, said signal corrector further comprising means to apply said drift compensating signal generated at times when said body has been at rest for more than said predetermined period of time to correct said drift sensitive signal.

40. An apparatus for simulating a virtual environment that is displayed to a user by an appropriate display device, said apparatus comprising:

a. a self contained orientation sensor to be attached to a body member of said user that has an orientation and a position relative to a reference frame, said sensor generating an orientation signal that:
 i. corresponds to at least two degrees of freedom of said orientation of said body member; and
 ii. is impervious to interference from electromagnetic, acoustic, optical and mechanical sources;

b. a position sensor that generates a position signal that corresponds to said position of said body member;

c. a mechanism for mounting said position and orientation sensors to said body member;

d. a virtual environment means for generating virtual environment signals that define, in part, a virtual environment;

e. a display that displays said virtual environment signals to said user; and f. means for coupling said position sensor and said orientation sensor to said virtual environment means.

41. The apparatus of claim 40, said orientation sensor comprising:

a. a first sensor that generates a drift sensitive orientation signal that corresponds to said at least two degrees of freedom of orientation and is subject to drift over time;

b. a second sensor that generates a drift compensating orientation signal that corresponds to said at least two degrees of freedom of orientation and which is relatively impervious to drift over time; and c. coupled to said first sensor and said second sensor, a signal corrector that generates a corrected orientation signal based on said drift sensitive and drift compensating orientation signals.

42. The apparatus of claim 41, said signal corrector comprising means to take into account characteristic features of human motion.

43. The apparatus of claim 42, said means to take into account characteristic features of human motion comprising means to determine times when said body has been at rest for more than a predetermined period of time.

44. The apparatus of claim 43, said signal corrector further comprising means to apply said drift compensating signal generated at times when said body has been at rest for more than said predetermined period of time to correct said drift sensitive signal.

* * * * *